United States Patent [19]
Patterson

[11] Patent Number: 5,869,240
[45] Date of Patent: Feb. 9, 1999

[54] METHODS AND APPARATUS FOR SEQUENCING POLYMERS WITH A STATISTICAL CERTAINTY USING MASS SPECTROMETRY

[75] Inventor: Dale H. Patterson, Nashua, N.H.

[73] Assignee: PerSeptive Biosystems, Inc., Framingham, Mass.

[21] Appl. No.: 447,175

[22] Filed: May 19, 1995

[51] Int. Cl.$^6$ .............................. C12Q 1/68; G06F 15/46; G06G 7/58; C07K 5/00
[52] U.S. Cl. ........................... 435/6; 435/91.1; 435/91.2; 435/18; 435/4; 422/62; 422/50; 364/496; 364/497; 364/498; 364/499; 530/300; 530/350; 536/23.1; 536/24.3
[58] Field of Search ................................. 435/6, 91.2, 18, 435/91.1, 9; 422/62, 50; 364/496, 497, 498, 499; 530/300; 536/23.1, 24.3

[56] References Cited

U.S. PATENT DOCUMENTS

| | | | |
|---|---|---|---|
| 5,064,754 | 11/1991 | Mills | 435/6 |
| 5,100,778 | 3/1992 | Rademacher et al. | 435/18 |
| 5,221,518 | 6/1993 | Mills | 422/62 |
| 5,382,513 | 1/1995 | Lam et al. | 435/7.1 |
| 5,622,824 | 4/1997 | Koster | 435/6 |

OTHER PUBLICATIONS

Chait et al. Science 262:89–92, 1993.
Bartlett–Jones et al. Rapid Comm. in Mass Spectrometry,8: 737–742, 1994.
Jue et al. Biochemistry 24: 162–70, 1985.
Eberhard, In Biology Laboratory,CBS College Publishing, Appendix B, 1987.
R.J. Colton, "Secondary Ion Mass Spectrometry: High–Mass Molecular and Cluster Ions" *Nucl. Instr. and Methods in Physics Res.* 218:276–286 (1983).
J.G. Van Raaphorst et al., "The Evaluation of Measurement Data in Thermal Ionisation Mass Spectrometry" *Intl. J. of Mass Spectrometry and Ion Physics* 31:65–69 (1979).
P. Roepstorff, "Mass Spectrometry of Proteins" *TRAC: Trends in Analytical Chemistry* 12(10):413–421 (1993).
Abstract: Database WPI, Section Ch. Week 9018, Derwent Publications Ltd., London, GB, Class B04, AN 90–137766, XPOO2014080 & SU,A,1 514 782 (1988).
International Search Report of corresponding PCT Application No. PCT/US96/07146 dated Oct. 4, 1996.

*Primary Examiner*—W. Gary Jones
*Assistant Examiner*—Dianne Rees
*Attorney, Agent, or Firm*—Testa, Hurwitz & Thibeault, LLP

[57] ABSTRACT

Integrated methods and apparatus for sequencing or identifying polymers by mass spectrometry with a statistical certainty. The methods involve integrating data obtained by mass spectrometry analysis of a series of polymer fragments and statistically comparing said data with hypothetical data corresponding to known sequences or identities.

47 Claims, 16 Drawing Sheets

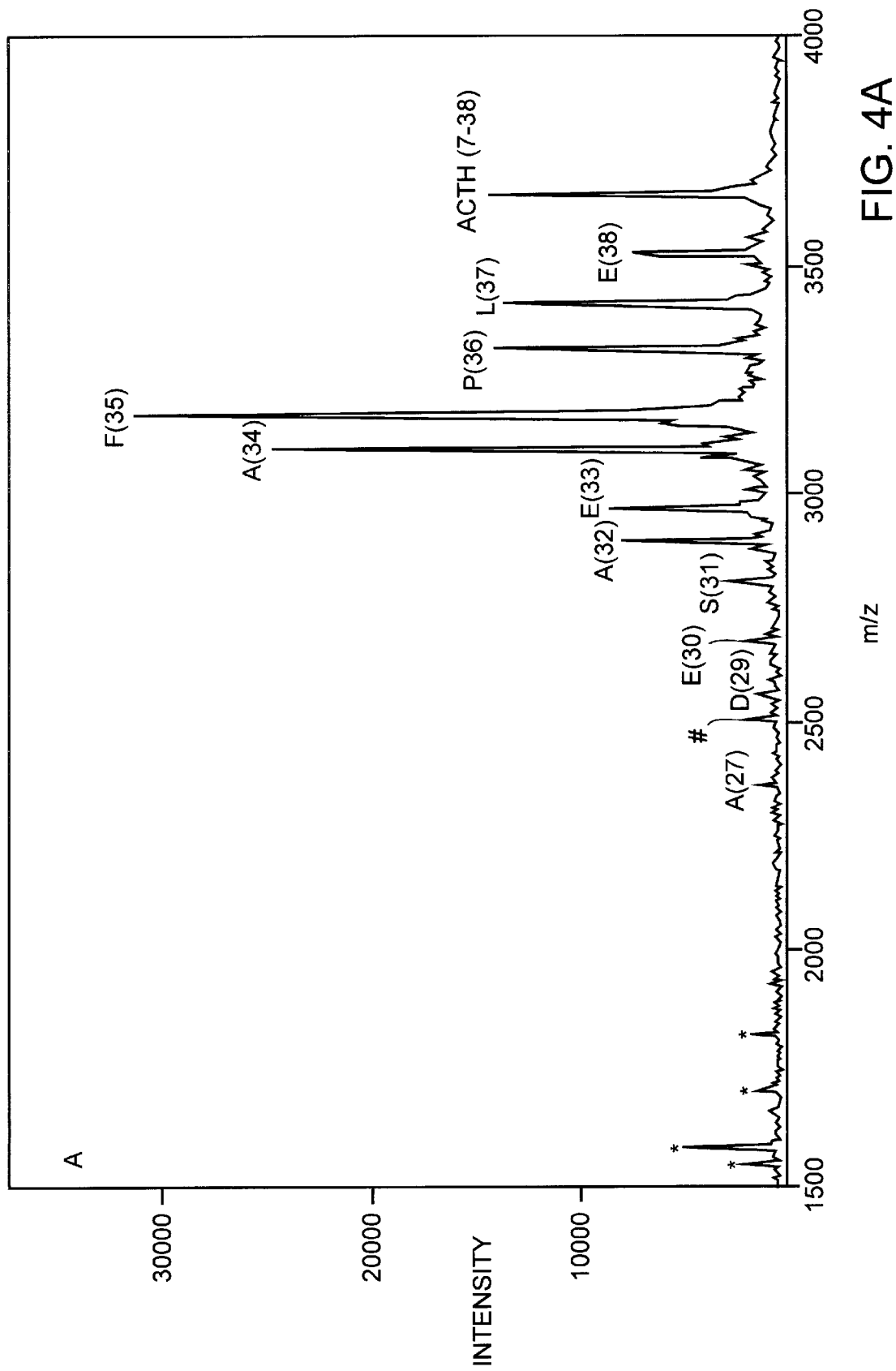

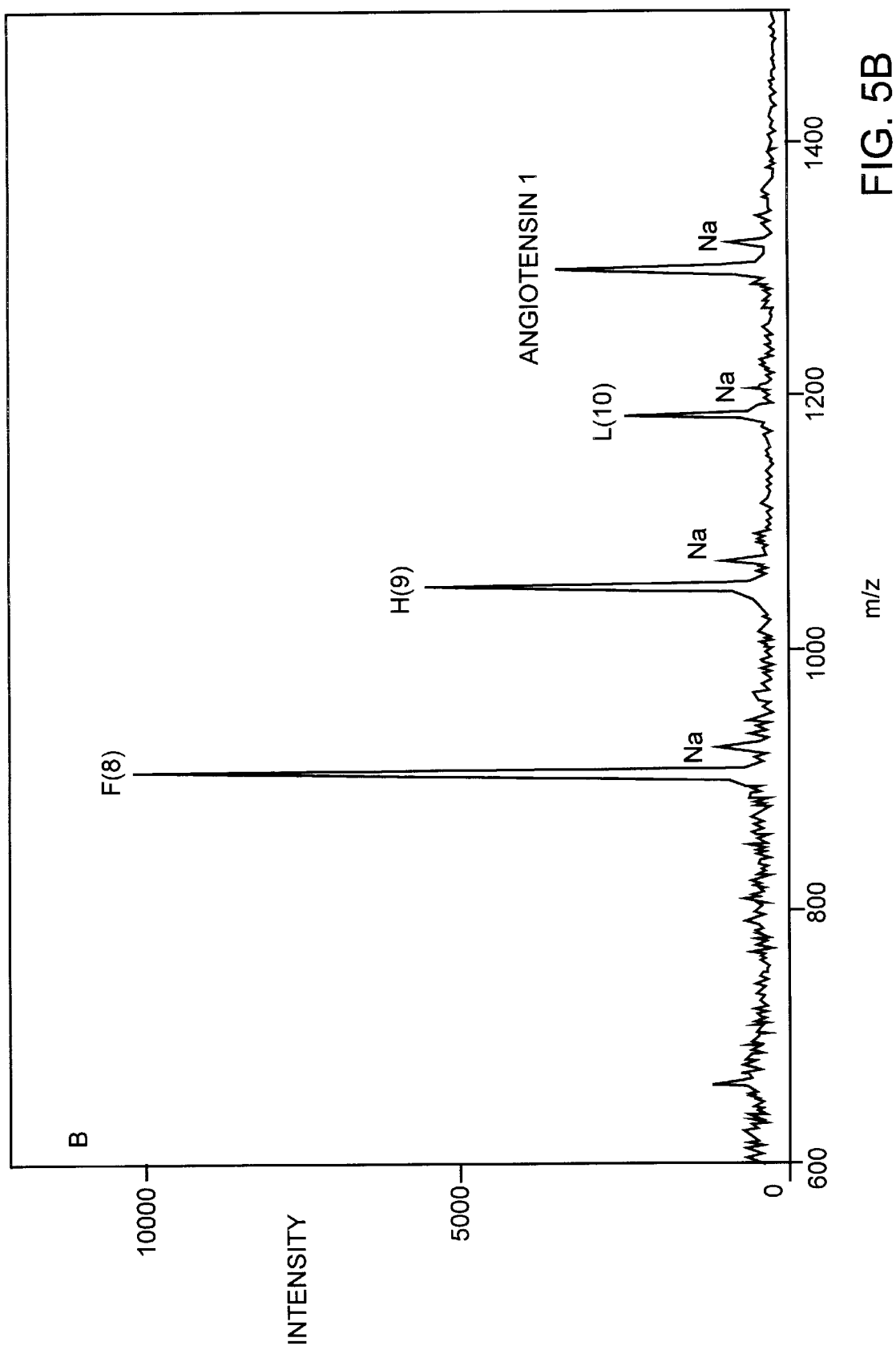

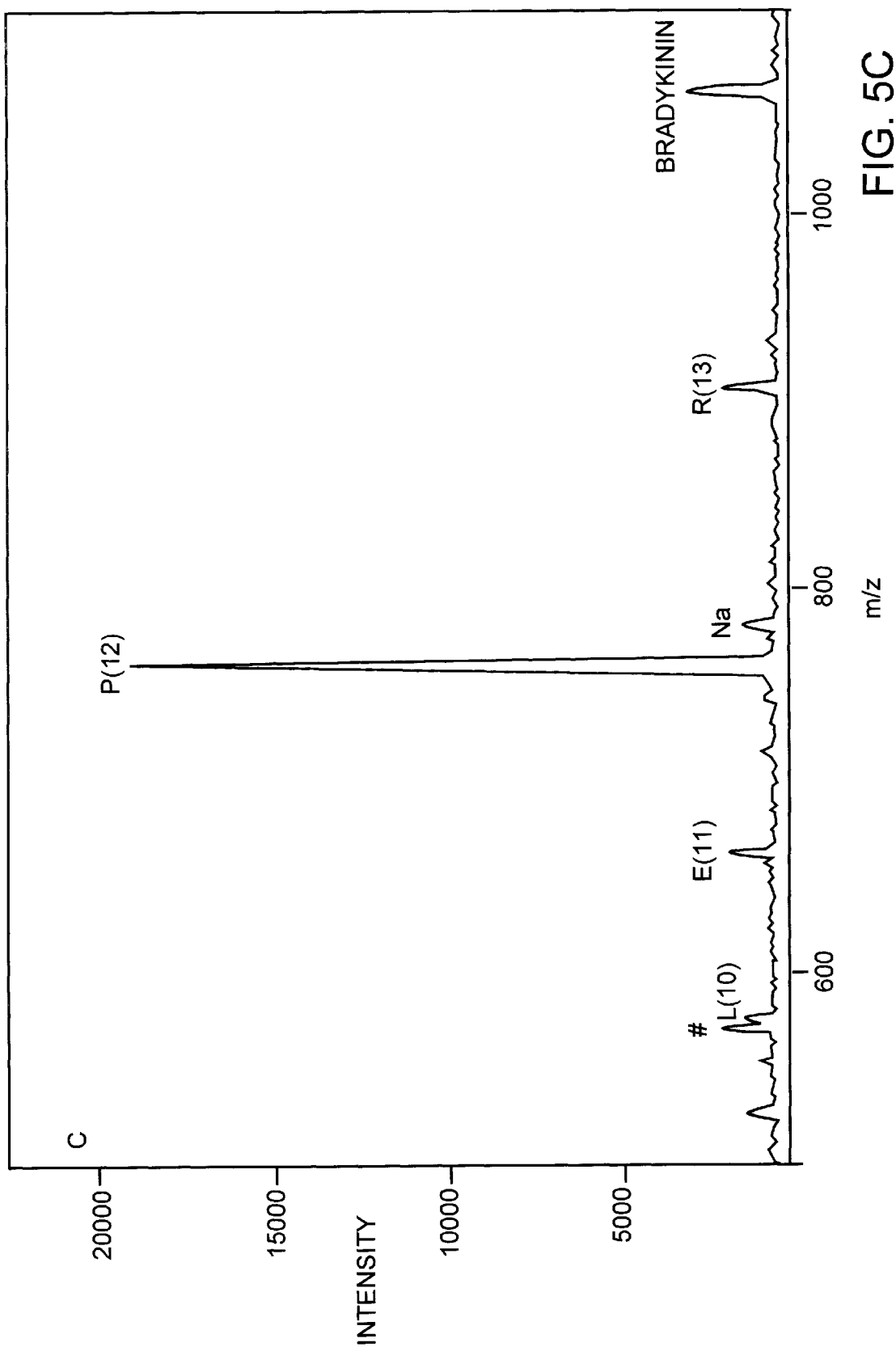

METHODS AND APPARATUS FOR SEQUENCING POLYMERS WITH A STATISTICAL CERTAINTY USING MASS SPECTROMETRY

BACKGROUND OF THE INVENTION

Biochemists frequently depend on reliable and fast determinations of the sequences of biological polymers. For example, sequence information is crucial in the research and development of peptide screens, genetic probes, gene mapping, and drug modeling, as well as for quality control of biological polymers when manufactured for diagnostic and/or therapeutic applications.

Various methods are known for sequencing polymers composed of essential biological building-blocks, such as amino acids and nucleotides. For example, existing methods for peptide sequence determination include the N-terminal chemistry of the Edman degradation, N- and C-terminal enzymatic methods, and C-terminal chemical methods. Existing methods for sequencing oligonucleotides include the Maxam-Gilbert base-specific chemical cleavage method and the enzymatic ladder synthesis with dideoxy base specific termination method. Each method possesses inherent limitations that preclude it being used exclusively for complete primary structure identification. To date, Edman sequencing and adaptations thereof are the most widely used tools for sequencing certain protein and peptides residue by residue, while the enzymatic synthesis method is preferred for sequencing oligonucleotides.

In the case of protein and peptide sequencing, C-terminal sequencing via chemical methods has proven particularly difficult while being only marginally effective, at best. (See, e.g., Spiess, J. (1986) *Methods of Protein Characterization: A Practical Handbook* (Shively, J. E. ed., Humana Press, N.J.) pp. 363–377; Tsugita et al. (1994) *J. Protein Chemistry* 13:476–479). Consequently, the C-terminus remains a region often not analyzed because of lack of a dependable method.

In the case of both peptides and oligonucleotides, an alternate approach to chemical sequencing is enzymatic cleavage sequencing. In the case of oligonucleotides, over 150 different enzymes have been isolated and found suitable for preparing oligonucleotide fragments. In the case of peptides, serine carboxypeptidases have proven popular over the last two decades because they offer a simple approach by which amino acids can be sequentially cleaved residue by residue from the C-terminus of a protein or a peptide. Carboxypeptidase Y (CPY), in particular, is an attractive enzyme because it non-specifically cleaves all residues from the C-terminus, including proline. (See, e.g., Breddam et al. (1987) *Carlsburg Res. Commun.* 52:55–63.)

Sequencing of peptides by carboxypeptidase digestion has traditionally been performed by a laborious, direct analysis of the released amino acids, residue by residue. Not only is this approach labor-intensive, but it is complicated by amino acid contaminants in the enzyme and protein/peptide solutions, as well as by enzyme autolysis. A further hindrance to any sequencing effort of this type is the absolute requirement for good kinetic information concerning the hydrolysis and liberation of each individual residue by the particular enzyme used.

With the advancement of mass spectrometric techniques capable of high mass analysis such as field desorption (Hong et al. (1983) *Biomed. Mass Spectrom.* 10:450–457), electrospray (Smith et al. (1993) 4 *Techniques Protein Chem.* 463–470), and thermospray (Stachowiak et al. (1988) *J. Am. Chem. Soc.* 110:1758–1765), it is possible to perform direct mass analysis on large biopolymers such as the peptide fragments resulting from CPY digestion in which the sequence order is preserved, circumventing the need for residue by residue amino acid analysis of the liberated amino acids. In this "ladder" sequencing approach, a sequence can be deduced, in the correct order, by simply calculating the mass differences between adjacent peptide peaks, the measured differences representing the loss of a particular amino acid residue.

More recently, matrix-assisted laser desorption ionization time-of-flight (MALDI-TOF) mass spectrometry also was shown to be suitable for ladder sequence analysis due to its high sensitivity, resolution, and mass accuracy. Chait et al. ((1993) 262 *Science* 89–92) exploited these assets of MALDI-TOF in the ladder sequencing of N-terminal ladders formed from partial blockage at each step of chemical digestion by the Edman degradation method. This approach, however, still suffers from the same limitations of traditional Edman chemistry including the complexity of the process which is time consuming and labor intensive and the lack of C-terminal information, however, it confirms the utility of MALDI-TOF for sequencing peptides using the peptide ladder scenario. Other researchers have also illustrated that carboxypeptidase digestion of peptides can be combined with MALDI-TOF to analyze the resulting mixture of truncated peptide. For example, eight consecutive amino acids have been sequenced from the C-terminus of human parathyroid hormone 1-34 fragment (Schar et al. (1991) *Chimia* 45:123–126). Additionally, carboxypeptidase digestion of peptides has been combined with other mass spectrometry methods such as plasma desorption (Wang et al. (1992) *Techniques Protein Chemistry III* (ed., R. H. Angeletti; Academic Press, N.Y.) pp. 503–515).

All of the above-described sequencing approaches, however, require preliminary optimization steps which are both tedious and time-consuming. Additionally, such preliminary optimization steps unnecessarily consume reagents as well as samples of polymer, usually available in limited quantities. Furthermore, frequently the above-described sequencing approaches ultimately rely on a single mass spectrum and a single mass-to-charge ratio data point, which can result in a statistically insufficient basis for determining a final polymer sequence.

It is an object of the present invention to provide methods and apparatus for sequencing polymers, particularly biopolymers, using mass spectrometry and time-independent/concentration-dependent hydrolysis of the polymer. It is an object of the present invention to also provide a rapid method for obtaining sequence information by circumventing the time-consuming optimization and method enhancement required by prior art methods. It is a further object of the present invention to provide sequence information using reduced quantities of total polymer by combining the sensitivity of mass spectrometry with elimination of sample loss by closely integrating hydrolysis with mass spectrometry analysis. It is another object of the present invention to provide a method for obtaining sequence information that incorporates a data interpretation strategy based on integrating mass-to-charge ratio data obtained from a plurality of parallel mass spectra.

SUMMARY OF THE INVENTION

Accordingly, the present invention is directed to an integrated method for sequencing polymers using information gathered by mass spectrometry, which substantially overcomes the problems encountered in the related art.

Additional features and advantages of the invention will be set forth in the description which follows, and in part will be apparent from the description, or may be learned by practice of the invention. The objectives and other advantages of the invention will be realized and attained by the methods, apparatus and kits of the invention, particularly pointed out in the written description and claims hereof.

To achieve these and other advantages and in accordance with the purpose of the invention as embodied and broadly described herein, the invention provides a method for obtaining sequence information about a polymer comprising a plurality of monomers of known mass. One skilled in the art first provides a set of fragments, created by the hydrolysis of the polymer, each set differing by one or more monomers. The difference between, x, the mass-to-charge ratio of at least one pair of fragments is determined. One then asserts a mean mass-to-charge, $\mu$, ratio which corresponds to the known mass-to-charge ratio of one or more different monomers. The asserted mean is compared with the measured difference to determine if the two values are statistically different with a desired confidence level. If there is a statistical difference, then the asserted mean difference is not assignable to the actual measured difference at the desired confidence level. In some embodiments, additional measurements of the difference between a pair of fragments are taken, to obtain a mean of the measured difference. The steps of the method are repeated until one has asserted all desired $\mu$s for a single difference between one pair of fragments. The method is repeated for additional pairs of fragments until the desired sequence information is obtained.

The claimed methods are applicable to any polymer, including biopolymers such as DNAs, RNAS, PNAs, proteins, peptides and carbohydrates, and modified forms of these polymers. The set of polymer fragments may be created by hydrolysis of the intermonomer bonds of the polymers. Thus, the invention also contemplates the inclusion of a hydrolyzing agent to cause the hydrolysis. Hydrolyzing agents may be enzymatic or an agent other than an enzyme, including for example, exohydrolases, and any combinations thereof.

In other embodiments the method of obtaining sequence information about a polymer includes providing a set of polymer fragments created by hydrolyzing said polymer, each fragment differing by one or more monomers of known mass; and measuring the mass-to-charge ratio difference x between a pair of fragments. Next, one asserts a mean difference $\mu$, which is related to a known mass-to-charge ratio of one or more monomers, and selects a desired confidence level for $\mu$. The step of measuring the mass-to-charge ratio difference x between a pair of fragments is repeated to obtain a number of measurements n, thereby to determine the measured mean mass-to-charge ratio difference $\bar{x}$ between the pair of fragments measured. One can then determine the standard deviation s of the measured mean mass-to-charge ratio difference $\bar{x}$ previously determined and calculate a test statistic $t_{calculated}$ with the following algorithm:

$$t_{calculated} = \frac{|\bar{x} - \mu|\sqrt{n}}{s}.$$

One can then repeat the steps of the method until all desired $\mu$s have been asserted for the mass-to-charge ratio difference between a pair of fragments. Sequence information for the polymer is obtained by repeating the steps of the method for additional pairs of fragments.

The apparatus and kits of the invention in various embodiments include either a mass spectrometer associated with a computer responsive thereto, or a computer associated with a mass spectrometer. In one embodiment the apparatus of the invention includes a mass spectrometer having a means for generating ions, a means for accelerating ions, and a means for determining ions. The mass spectrometer is associated with a computer which is responsive to the mass spectrometer, wherein the computer has the means for performing the methods of the invention.

The apparatus of the invention in other embodiments includes a computer readable disc having thereon the information necessary to, in combination with a mass spectrometer, perform the methods of the invention. In other embodiments, the apparatus includes the computer itself, having means for performing the methods of the invention.

It is to be understood that both the foregoing general description and the following detailed description are exemplary and explanatory and are intended to provide further explanation of the invention as claimed. The accompanying drawings are included to provide a further understanding of the invention and are incorporated in and constitute a part of this specification, illustrate several embodiments of the invention, and together with the description serve to explain the principles of the invention.

BRIEF DESCRIPTION OF THE DRAWINGS

FIGS. 4A and 4B are various is a MALDI spectra of on-plate concentration-dependent CPY digestions of ACTH 7-38 fragment.

DETAILED DESCRIPTION

Figure 1:
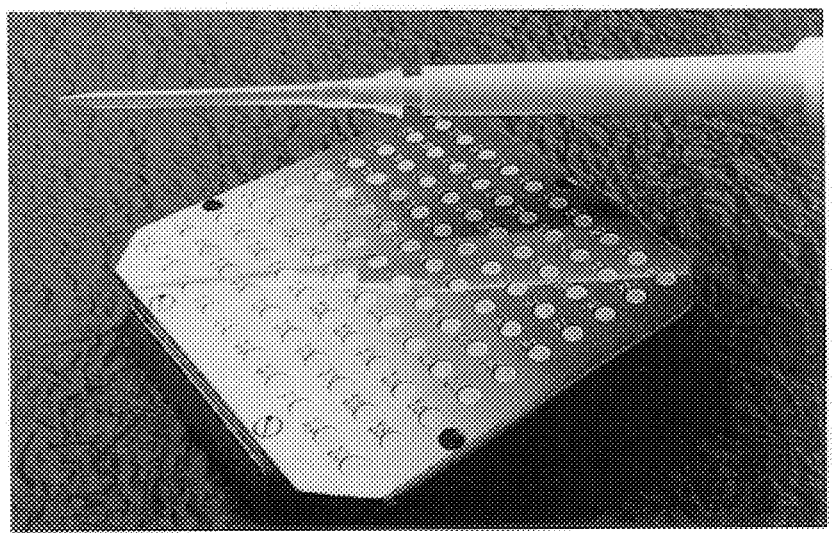
FIG. 1 is an exemplary sample plate for MALDI analysis.

Reference will now be made in detail to the present preferred embodiments of the invention, examples of which are illustrated in the accompanying drawings.

The present invention provides an integrated strategy for obtaining sequence information about a polymer comprising a plurality of monomers of known mass. Specifically, using sets of polymer fragments and mass spectrometry, the invention provides a method of interpretation of sequence data obtained by mass spectrometry, which allows the rapid, automated and cost effective sequencing of polymers with a statistical certainty.

As used herein, a "polymer" is intended to mean any moiety comprising a series of different monomers suitable for use in the method of the instant invention. That is, any moiety comprising a series of different monomers whose intermonomer bonds are susceptible to hydrolysis are suitable for use in the method disclosed herein. For example, a peptide is a polymer made up of particular monomers, i.e., amino acids, which can be hydrolyzed by either enzymatic or chemical agents. Similarly, a DNA is a polymer made up of other monomers, i.e., bases, which can be hydrolyzed by a variety of agents.

A polymer can be a naturally-occurring moiety as well as a synthetically-produced moiety. In a currently preferred embodiment, the polymer is a biopolymer selected from, but not limited to, the following group: proteins, peptides, DNAs, RNAs, PNAs (peptide nucleic acids), carbohydrates and modified forms thereof.

"Sequence information" as used herein is intended to mean any information relating to the primary arrangement of the series of different monomers within the polymer, or within portions thereof. Sequence information includes information relating to the chemical identity of the different monomers, as well as their particular position within the polymer. Polymers with known primary sequences, as well as polymers with unknown primary sequences, are suitable for use in the methods of the instant invention. It is contemplated that sequence information relating to terminal monomers as well as internal monomers can be obtained using the methods disclosed herein.

In certain applications, sequence information can be obtained using a sample of an intact, complete polymer. In other applications, sequence information can be obtained using a sample containing less than the intact complete polymer, for example, polymer fragments. Such fragments can be naturally-occurring, artifacts of isolation and purification, and/or generated in vitro by the skilled artisan. Additionally, polymer fragments can be initially derived from and prepared by a variety of fractionation and separation methods, such as high performance liquid chromatography, prior to use with the methods of the instant invention.

The sets of polymer fragments can be created by any method. The claimed methods contemplate the step of hydrolyzing the polymer with a hydrolyzing agent to obtain the fragments, or synthesizing fragments, as well as merely providing a set of fragments which have been obtained previously. As used herein, the term "hydrolyzing agent" is intended to mean any agent capable of disrupting inter-monomer bonds within a particular polymer. That is, any agent which can interrupt the primary sequence of a polymer is suitable for use in the methods disclosed herein. Hydrolyzing agents can act by liberating monomers at either termini of the polymer, or by breaking internal bonds thereby generating fragments or portions of the subject polymer. Generally, a preferred hydrolyzing agent interrupts the primary sequence by cleaving before or after a specific monomer(s); that is, the agent specifically interacts with the polymer at a particular monomer or particular sequence of monomers recognized by the agent as the preferred hydrolysis site within the polymer. All of the currently preferred hydrolyzing agents described herein are commercially available from reagent suppliers such as Sigma Chemicals (St. Louis, Mo.). Preferred exohydrolases include, but are not limited to , exonucleases, exoglycosylases, exopeptidases, carboxypeptidases (i.e. Y, A, B, and P), aminopeptidase 1, LAP, proline aminodipeptidase and cathepsin C. Preferred exoglycosidases include but are not limited to α-Mannosidese I, α-Mannosidese, β-Hexosaminidese, β-Galactosidase, α-Fucosidase I and II, α-Galactosidase, α-Neuraminidase and, α-Glucosidase I and II. Preferred exonucleases include, but are not limited to Exonuclease, λ-exonuclease, t7 Gene 1 exonuclease, exonuclease III, Exonuclease I, Exonuclease V, Exnonuclease II, DNA Polymerase II.

It may be preferable to use a combination of hydrolyzing agents, for example a combination of an enzymatic agent with an agent which is not an enzyme.

The claimed invention can be applied to the sequencing of any natural biopolymer such as proteins, peptides, nucleic acids, carbohydrates, etc., as well as synthetic biopolymers such as PNA and phosphotiolated nucleic acids. The ladders could conceivably be created enzymatically using exohydrolases, endohydrolases or the Sanger method and/or chemically by truncation synthesis or failure sequencing.

It is preferable to use on-plate digestion and interpretation of peptide ladders created from carboxypeptidase Y, carboxypeptidase P and aminopeptidase I digestions of numerous peptides. In accordance with the instant invention, such exohydrolases generate a series of hydrolyzed fragments comprising a sequence-defining "ladder" of the polymer. That is, these agents generate a series of hydrolyzed fragments, each hydrolyzed fragment within the series being a "ladder element," which collectively comprise a sequence-defining "ladder" of the polymer. Ladder elements represent hydrolyzed fragments from which monomers have been consecutively and/or progressively liberated by the exohydrolase acting at one or the other of the polymer's termini. Accordingly, ladder elements are truncated hydrolyzed polymer fragments, and ladders per se are concatenations of these collective truncated hydrolyzed polymer fragments. In this manner, for example, sequence information relating to the amino acid sequence of a protein can be obtained using carboxypeptidase Y, an agent which acts at the carboxy terminus. By using the methods disclosed herein to generate a series of protein hydrolysates related one to the other by consecutive, repetitive liberation of amino acid residues, the skilled artisan can reconstruct the primary sequence of the intact protein polymer as described in further detail below.

Similarly, hydrolyzing agents other than exohydrolases which also act at one or the other of a polymer's termini generate ladder elements which collectively comprise a series of sequence-defining ladders. For example, the well-known Edman degradation technique and associated reagents can be adapted for use with the methods of the instant invention for this purpose. Thus the above-described subtractive-type sequencing method, through which repetitive removal of successive amino-terminal residues from a protein polymer can occur, can also be accomplished with hydrolyzing agents other than enzymes as disclosed herein.

As previously described, sequence information can also be obtained using hydrolyzing agents which act to disrupt internal inter-monomer bonds. For example, an endohydrolase can generate a series of hydrolyzed fragments useful ultimately in constructing a "map" of the polymer. That is, this agent generates a series of related hydrolyzed fragments which collectively contribute information to a sequence-defining "map" of the polymer. For example, peptide maps can be generated by using trypsin endohydrolysis in tandem with cyanogen bromide endohydrolysis to obtain hydrolyzed fragments with over-lapping amino acid sequences. Such overlapping fragments are useful for reconstructing ultimately the entire amino acid sequence of the intact polymer. For example, this combination of hydrolyzing agents generates a useful plurality of series of hydrolyzed fragments because trypsin specifically catalyzes hydrolysis of only those peptide bonds in which the carboxyl group is contributed by either a lysine or an arginine monomer, while cyanogen bromide cleaves only those peptide bonds in which the carbonyl group is contributed by methionine monomers. Thus, by using trypsin and cyanogen bromide hydrolysis in tandem, one can obtain two different series of hydrolyzed "mapping" fragments.

These series of mapping fragments are then examined by mass spectrometry to identify specific hydrolysates from the second cyanogen bromide hydrolysis whose amino acid sequences establish continuity with and/or overlaps between the specific hydrolysates from the first hydrolysis with trypsin. Overlapping sequences from the second hydrolysis provide information about the correct order of the hydrolyzed fragments produced by the first trypsin hydrolysis. While these general principles of peptide mapping are well-known in the prior art, utilizing these principles to obtain sequence information by mass spectrometry as disclosed herein has heretofore been unknown in the art.

It will be obvious to the skilled artisan that certain sequencing determinations will be best accomplished using the above-described ladder scenario, while others will be better suited to the mapping scenario. In some situations, a combination of the ladder and mapping sequencing methodologies taught herein will provide optimum sequence information. Using only routine experimentation, the skilled artisan will be able to obtain optimum sequence information using the ladder and/or mapping methods in conjunction with mass spectrometry analysis of a plurality of the series of hydrolyzed polymer fragments.

The claimed invention may be practiced using any type of mass spectrometry known in the art. Any manner of ion formation can be adapted for obtaining mass-to-charge ratio data, including but not limited to: matrix-assisted laser desorption ionization, plasma desorption ionization, electrospray ionization, thermospray ionization, and fast atom bombardment ionization. Additionally, any mode of mass analysis is suitable for use with the instant invention including but not limited to: time-of-flight, quadrapole, ion trap, and sector analysis. A currently preferred mass spectrometer instrument is an improved time-of-flight instrument which allows independent control of potential on sample and extraction elements, as described in copending U.S. Ser. No. 08/446055 (Atty. Docket No. SYP-115) filed on even date herewith and which is herein incorporated by reference. The mass spectrometers used in the invention include a means to generate ions, a means to accelerate ions, and, a means to detect ions. Any ionization method may be used, for example, desorption, negative ion fast atom bombardment, matrix- assisted laser desorption and electrospray ionization. It is preferable to use matrix-assisted laser desorption mass spectrometry.

Peptide ladders may be created using the traditional approach in which aliquots of samples are removed at selected time intervals from enzymatic digests. However, this method of development may be slow and labor intensive as the removal and analysis of many aliquots is often necessary.

Solution-phase digestions suffer from a number of disadvantages. A large amount of time, enzyme and peptide is required for method development in order to obtain significant digestion in a short amount of time while preserving all possible sequence information. For each peptide from which sequence information is to be derived, some time-consuming method development must be performed since a set of optimum conditions for one peptide is not likely to be useful for another peptide given the composition-dependent hydrolysis rates of CPY. An alternative strategy is to perform the digestion on the MALDI sample surface.

Additionally, solution phase digestions by hydrolysis suffer from a number of disadvantages. A large amount of time, enzyme and peptide is required for method development in order to obtain significant digestion in a short amount of time while preserving all possible sequence information. For each peptide from which sequence information is to be derived, some time-consuming method development must be performed, since a set of optimum conditions for one peptide is not likely to be useful for another peptide, because the hydrolysis rates of various peptides are composition dependent.

In another aspect, the instant invention provides a mass spectrometer sample holder. The instant sample holder is useful for adapting any mass spectrometer apparatus for obtaining sequence information in accordance with the disclosed methods. In one currently preferred embodiment, the sample holder has a planar solid surface on which is disposed hydrolyzing agent. In another currently preferred embodiment, the sample holder has the form of a probe useful in certain mass spectrometer apparatus. In all embodiments of the sample holder, the agent can be in dehydrated and/or immobilized form. The agent can be disposed in separate discrete zones of differing amounts, or in a non-discrete gradient. Alternatively, the agent can be disposed in a constant amount on the surface of the sample holder. In other embodiments, the sample holder has a light-absorbent matrix disposed on its surface; this can be with or without hydrolyzing agent.

It is preferable in some embodiments to obtain sets of fragments of the polymer to be sequenced by hydrolyzing the polymer on a reaction surface having one or more different amounts of a hydrolyzing agent. The hydrolyzing agent hydrolyzes the polymer by breaking the intermonomer bonds. In a most preferred embodiment, a hydrolyzing agent is provided in spatially separate differing amounts on the reaction surface such that parallel concentration dependent hydrolysis occurs. This method is described in detail and claimed in a copending application, identified by attorney docket No. SYP-115, U.S. Ser. No. 08/446055, filed concurrently herewith and specifically incorporated herein by reference.

Briefly, in some embodiments, a series of concentrations of hydrolyzing agent can be dispersed across a row of the $\mu$L wells of the sample plate of the Voyager™ MALDI-TOF Biospectrometry Workstation, available from PerSeptive Biosystems, Inc. Following passive or active evaporation, and/or addition of a PH shifting reagent, matrix may be added to each well and the sample plate "read" with a MALDI-TOF mass spectrometer. Although time-dependent and concentration-dependent digestions should yield analogous sequence information, it is preferred to use a concentration-dependent approach because it is easily automated, all samples are ready at the same time, and less sample material is lost due to transfer from reaction vessels to the analysis plate. It is therefore preferred to use concentration-dependent on plate hydrolysis , with subsequent analysis on a MALDI mass spec, because it requires only a few pmol of total peptide as a combined result of the sensitivity of MALDI and no sample loss upon moving from digestion to analysis.

When obtaining sequence information by MALDI, matrix may be added to the sample fragments at any time prior to measuring the mass-to-charge ratios. For example, matrix may be preloaded onto the reaction surface, or, alternatively, added to the hydrolyzing mixture, prior to, during, or after hydrolysis. Additionally, it may be desirable to add excipients. Mass shifting moieties can be added if desired, for example moieties whose reaction products include, alkyl, aryl, acyl thioacyl, oxycarbonyl, carbamyl, thiocarbomyl, sulfonyl, imino, guanyl, ureido and/or silyl. Similarly, one may add moieties to improve ionization, i.e. moieties whose reaction products include amino, quarternary amino, pyridino, imidino, guanidino, oxonium, and/or sulfonium.

The claimed invention is an integrated method for generating sequence information about a polymer comprising a plurality of monomers of known mass. The method involves the interpretation of mass-to-charge ratio data of a set of fragments obtained from the polymer, to statistically identify monomer differences between pairs of fragments. In the past, known molecular masses have been compared to MALDI derived masses for a few mass measurements, and researchers have attempted to make general statements on the instrumental mass accuracy.

In general, the methods of the claimed invention involve multiple integrated steps which may be automated according to the invention.

After providing a set of polymer fragments, each differing by one or more monomers, the difference, x, between the mass-to-charge ratio of at least one pair of fragments is measured. Next, one asserts a mean difference $\mu$ between the mass-to-charge ratio of the pair of fragments measured, wherein $\mu$ corresponds to a known mass-to-charge ratio of one or more differing monomers. One then analyses x to determine if it is statistically different from the $\mu$ with a selected confidence level.

If one determines that a statistical difference does exist, then the asserted $\mu$ is not assignable to the mass difference x with the selected confidence level.

The steps described above are repeated until all desired $\mu$s have been asserted, and then can be repeated for additional pairs of fragments.

In certain embodiments, the analysis to determine if x is statistically different from $\mu$ comprises taking repeated measurements of x, a number of times n, to determine a measured mean mass-to-charge ratio difference $\bar{x}$ between at least one pair of fragments. A standard deviation s of the measured mean $\bar{x}$ can then be determined, and the measured mean $\bar{x}$ compared to the asserted mean $\mu$ to determine if they are statistically different with the desired confidence level.

In certain embodiments of the present invention, a set of polymer fragments are obtained, either by on plate digestion, or from an external source, and one or more measurements of the mass-to-charge ratio of a pair of the fragments are taken. Peaks representing the loss of one or monomers can be analyzed using t-statistics to allow assignments to be made with a desired confidence interval. The two-tailed t-test for one experimental mean, $$t_{calculated} = \frac{|\bar{x} - \mu|\sqrt{n}}{s}$$

where x is the experimental mean mass difference, $\mu$ is the asserted mass difference, n is the number of replicates performed and s is the experimental standard deviation of the mean, is applied. All conceivable masses (single residue, di-residue, tri-residue . . . etc., as well as modified residue masses) are used as $\mu$, the asserted mass, to generate a list of $t_{calculated}$ values that are then compared against tabulated values for given confidence intervals. All masses that do not statistically differ from the asserted mass, $t_{calculated} < t_{table}$, are statistically assigned to that residue(s) at the given level of confidence. This information can be used to check hypothesized compositions or used to search a database for a sequence.

When performing database searching, these levels of confidence can be used in the search algorithm as a tool to aid in obtaining quality "hits."

Ultimately, this technique is to be used for the sequence determination of peptides of unknown sequence. By comparing the known molecular masses to the MALDI derived masses for a few mass measurements, researchers have attempted to make general statements of instrumental mass accuracy (e.g. better than 0.1%). Ascribing this mass accuracy to any individual mass measurement for the purpose of residue assignment holds no statistical validity, therefore making true residue assignment and direct application to unknowns difficult. In order to call amino acid sequences by ladder sequencing/MALDI strategies, statistical levels of confidence must be placed on residue assignments.

The claimed invention also relates to obtaining information about the identity of a polymer by providing a set of polymer fragments created by the endohydrolysis of a polymer. Typically, the use of an endohydrolase creates a set of fragments defining a map of said polymer, as discussed above. The mass-to-charge ratio of the fragments is measured, and a hypothetical identity is asserted for the fragment measured. The hypothetical identity corresponds to a known identity of a fragment of a reference polymer. Information on reference polymers is easily included in a database to be used with this method. After selecting a desired confidence level, one determines whether the mass-to-charge ratio of the asserted hypothetical fragment is statistically different from the mass-to-charge ratio of the asserted hypothetical fragment. If it is, then the steps are repeated for different additional hypothetical fragments. This method is repeated until sufficient information is obtained about the fragments that one can identify the polymer with a desired confidence level. Thus, when one is working with maps, one essentially determines whether the measured masses of fragments of the polymer correspond to hypothetical masses of fragments of a known polymer with enough certainty to identify the polymer. It is preferable that the hypothetical identities which are asserted correspond to a known identity derived from a computer database of known sequences.

The methods of the invention also contemplate providing multiple different sets of fragments of the same polymer, i.e. maps and ladders, to obtain the maximum amount of sequence information possible.

The claimed invention, in other embodiments, relates to an apparatus and/or kit for performing the methods above. In one embodiment the apparatus of the invention for obtaining sequence information about a polymer comprises a mass spectrometer having a means for generation of ions from a sample, a means for acceleration of ions generated, and a detection means. These basic components are available in numerous embodiments, and therefore, the invention is not limited to a particular type of mass spectrometer. The apparatus additionally comprises a computer responsive to the mass spectrometer comprising a means for determining the mass to charge ratio difference x between a pair of polymer fragments; a means for asserting a mean difference $\mu$ between the mass-to-charge ratio of the pair of fragments, wherein $\mu$ corresponds to a known mass-to-charge ratio of one or more monomers; and a means for analyzing x to determine if it is statistically different from $\mu$ with the desired confidence level, and a means for determining when the desired number of possible $\mu$s have been asserted.

Additionally, the information necessary for the claimed methods can be incorporated onto a computer-readable disc, which can render a computer responsive to a mass spectrometer for performing the analysis. Claimed software will automate the process of acquiring and interpreting the data in an intelligent fashion using software feedback control. The data interpretation software would control the number of acquisitions that are required to statistically differentiate multiple candidates for an amino acid assignment. The operator would have control of specifying to what minimum statistical level of confidence the assignment(s) must meet.

EXPERIMENTAL

Example 1. Materials and Methods (a) Solution-Phase Digestion of ACTH 7-38 Fragment For a time course digestion, 500 pmol of synthetic human adrenocorticotropic hormone (ACTH) fragment (7-38) [Phe Arg Trp Gly Lys Pro Val Gly Lys Lys Arg Arg Pro Val Lys Val Tyr Pro Asn Gly Ala Glu Asp Glu Ser Ala Glu Ala Phe Pro Leu Glu] (SEQ ID NO:22) [FRWGKPVGKKRRPVKVYPNGAEDESAEAFPLE] from Sigma Chemical Company (St. Louis, Mo.), previously dried down in a 0.5 mL eppendorf vial, was resuspended with 33.3 μL of HPLC grade water (J. T. Baker, Phillipsburg, N.J.). In a previously dried down 0.5 mL eppendorf tube, 3.05 units (one unit hydrolyzes 1.0 μmol N-CBZ-phe-ala to N-CBZ-phenylanine+alanine per minute at pH=6.75 and 25° C.) of carboxypeptidase Y from bakers yeast (E.C. 3.416.1), purchased from Sigma, was resuspended with 610 μL of HPLC grade water. To 20 μL of the ACTH 7-38 fragment solution was added 10 μL of the CPY solution to initiate the reaction. The final concentrations were 10 pmol/μL ACTH and $1.67 \times 10^{-3}$ units/μL CPY yielding an enzyme-to-substrate ratio of $1.67 \times 10^8$ units CPY/mol ACTH (1:37 molar ratio assuming CPY MW=61,000). Aliquots of 1 μL were taken from the reaction vial at reaction times of 15 s, 60 s, 75 s, 105 s, 2 min, 135 s, 4 min, 5 min, 6 min, 7 min, 8 min, 9 min, 10 min, 15 min and 25 min. At 25 min, 15 μL of $5 \times 10^{-3}$ units/μL CPY was added to the reaction vial. Aliquots of 2 μL were removed at total reaction times of 1 hr and 24 hr. The reaction proceeded at room temperature until 2 min when the temperature was elevated to 37° C. All aliquots were added to 9 μL of the MALDI matrix, α-cyano-4-hydroxy cinnamic acid (CHCA) from Sigma, at a concentration of 5 mg/mL in 1:1 acetonitrile (ACN):0.1% trifluoroacetic acid (TFA) with the exception of the 1 hr and 24 hr aliquots were added to 8 μL of the matrix. The final total peptide concentrations of the ACTH digestion aliquots in the matrix solutions were 1 pmol/μL. A pooled peptide solution was prepared by combining 2 μL of the 15 s, 105 s, 6 min and 25 min aliquots. Into individual μL wells on the MALDI sample plate, 1 μL of each aliquot solution was placed and allowed to evaporate to dryness before insertion into the mass spectrometer.

(b) On-Plate Digestions:

All on-plate digestions were performed by pipetting 0.5 μL of the peptide at a concentration of 1 pmol/μL into each of ten 1 μL wells across one row of a sample plate configured similarly to the sample plate manufactured and supplied by PerSeptive BioSystems, Inc. of Framingham, Mass. and adapted for use with their trademarked mass spectrometry apparatus known as Voyager™. All peptides listed in Table 1 were purchased from Sigma and were of the highest purity offered. To initiate the reaction in the first well, 0.5 μL of 0.0122 units/μL CPY was added. To the subsequent 9 wells was added CPY at concentrations of $6.10 \times 10^{-3}$, $3.05 \times 10^{-3}$, $1.53 \times 10^{-3}$, $6.10 \times 10^{-4}$, $3.05 \times 10^{-4}$, $1.53 \times 10^{-4}$, $7.63 \times 10^{-5}$, $3.81 \times 10^{-5}$ and 0 units/μL, respectively. Mixing was assured in each well by pulling the 1 μL reaction back and forth through the pipet tip. The reaction was allowed to proceed at room temperature until the 1 μL total volume evaporated on the plate (approximately 10 min). At such time, 1 μL of 5 mg/mL CHCA in 1:1 ACN:0.1% TFA was added to each well, with no further mixing, and allowed to evaporate for approximately 10 min before mass analysis.

(c) MALDI-TOF Mass Spectrometry:

MALDI-TOF mass analysis was performed using the VOYAGER™ BIOSPECTROMETRY™ Workstation (PerSeptive Biosystems, Cambridge, Mass.). A 28.125 KV potential gradient was applied across the source containing the sample plate and an ion optic accelerator plate in order to introduce the positively charged ions to the 1.2 m linear flight tube for mass analysis. For the data acquisition of the ACTH 7-38 fragment and glucagon digests, a low mass gate was used to prevent the matrix ions from striking the detector plate. For the application of the low mass gate, the guide wire was pulsed for a brief period deflecting the low mass ions (approximately <1000 daltons). All other spectra were recorded with the low mass gate off. To enhance the signal-to-noise ratio, 64–128 single shots from the nitrogen laser (337 nm) were averaged for each mass spectrum. The data presented herein were smoothed using an 11 point Savitsky-Golay second order filter. All data was calibrated using an external calibration standard mixture of bradykinin ($MH^+$=1061.2) and insulin B-chain, oxidized ($MH^+$=3496.9) (both purchased from Sigma) at concentrations of 1 pmol/μL in the 5 mg/mL CHCA matrix solution.

(d) Statistical Mass Assignments:

As described in further detail below, the statistical protocol disclosed herein uses the equation for the two-tailed t-test:

$$t_{calculated} = \frac{\bar{x} - \mu/\sqrt{n}}{s}$$

where $\bar{x}$ is the average experimental mean, μ is the asserted mean, n is the number of replicates and S is the experimental standard deviation. For the assignment of residues to experimentally derived Δ masses, a $t_{calculated}$ for each asserted mean mass (each possible amino acid assignment) was compared to the tabulated value for a given confidence interval. A $t_{calculated} > t_{table}$ indicated that the experimental mass came from a population possessing a different mean than the asserted mass at the given confidence level.

Figure 2A:
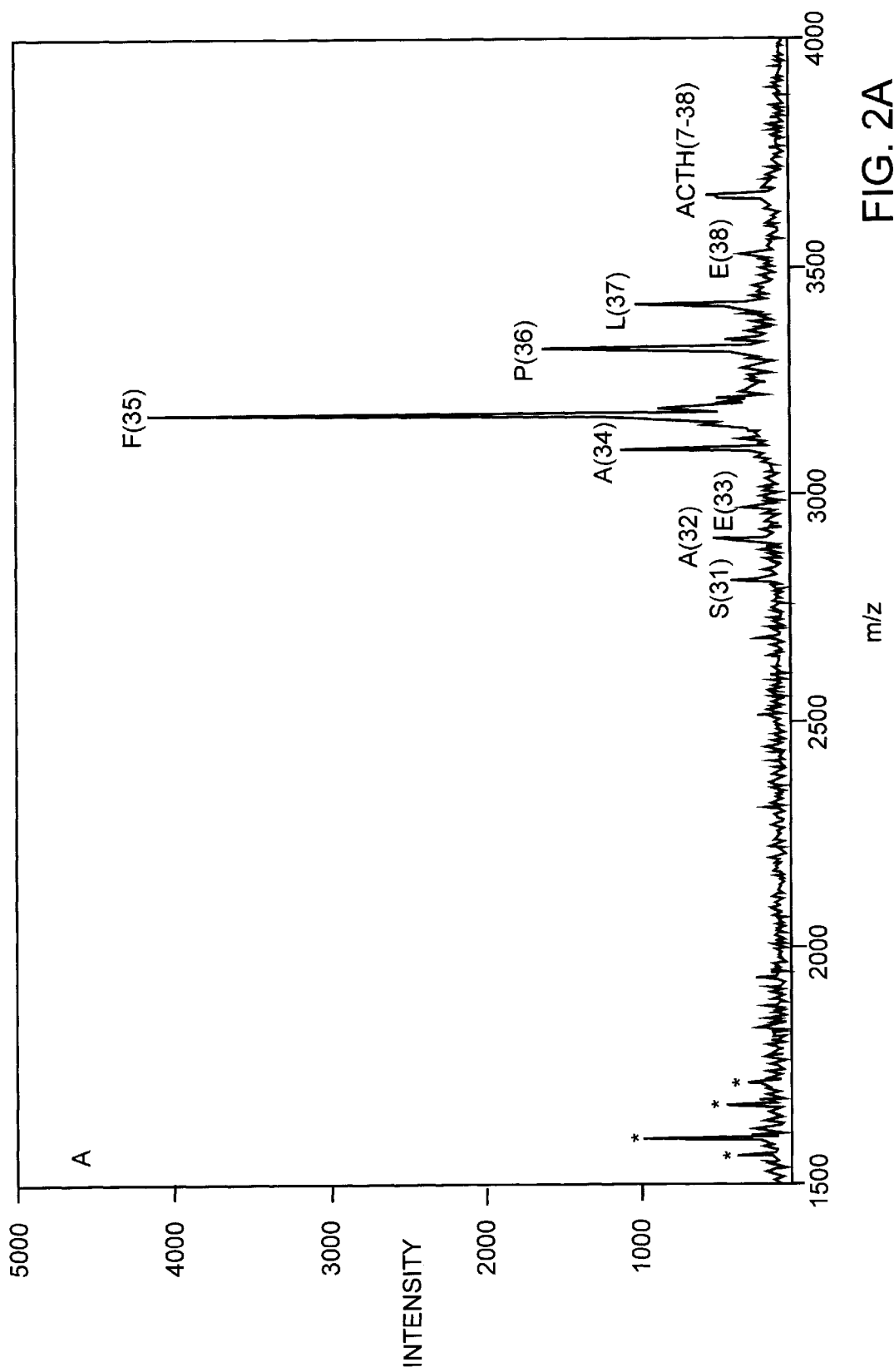
FIG. 2 is a MALDI spectra of the 1 min (A), 5 min (B) and 25 min (C) aliquots from a time-dependent CPY digestion of ACTH 7-38 fragment [Phe Arg Trp Gly Lys Pro Val Gly Lys Lys Arg Arg Pro Val Lys Val Tyr Pro Asn Gly AlaGlu Ser Ala Glu Ala Pre Prolev Glu]. (SEQ. ID NO.22)
Figure 2B:
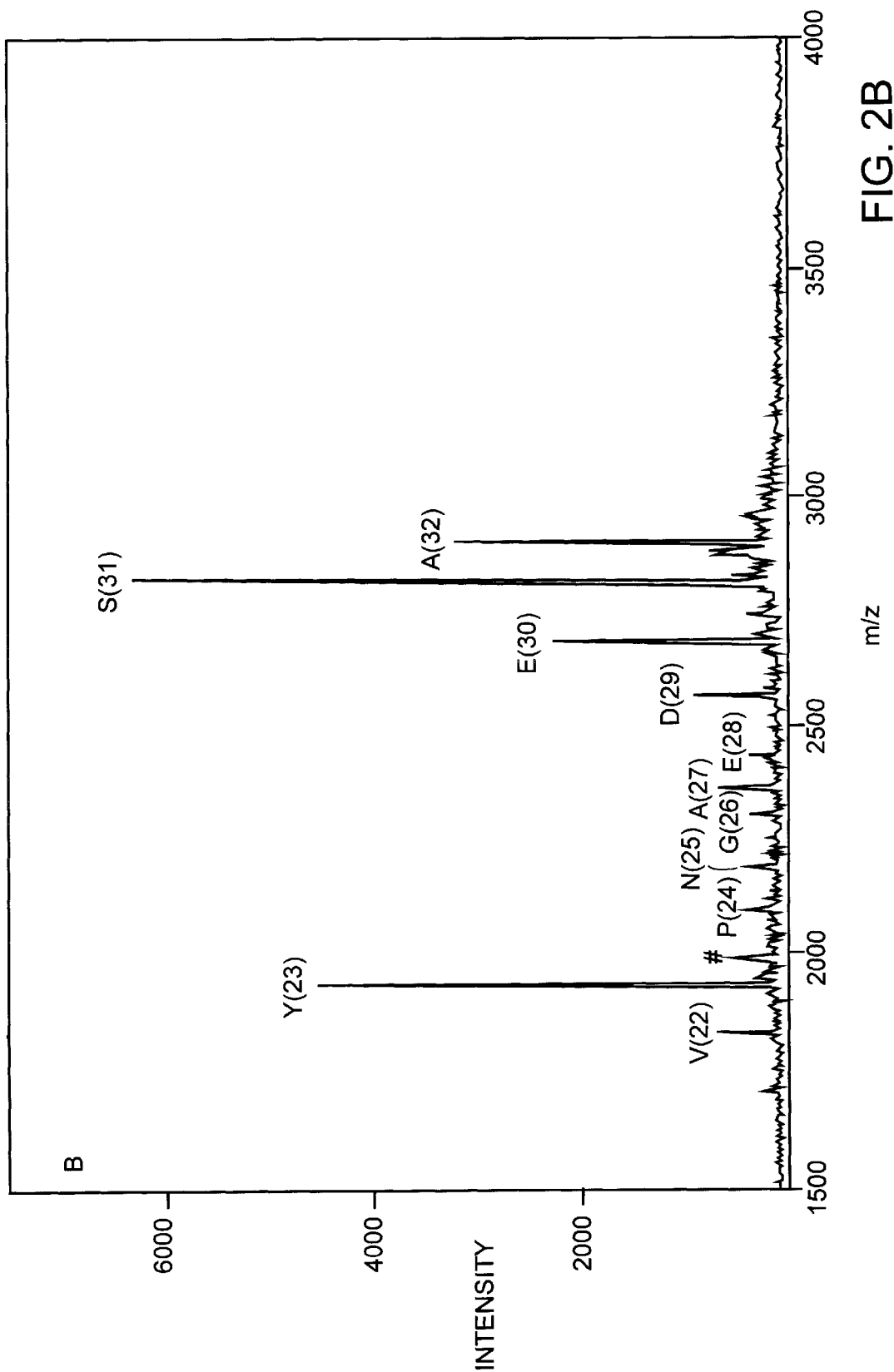

Example 2. Sequencing of Biopolymers (a) Solution-Phase Sequencing:

FIG. 2 illustrates the MALDI spectra of the 1 min, 5 min and 25 min time aliquots that were removed from a solution-phase time-dependent CPY digestion of ACTH 7-38 fragment. The nomenclature of the peak labels denotes the peptide populations resulting from the loss of the indicated amino acids. Peaks representing the loss of 19 amino acids from the C-terminus are observed. The symbol * indicates doubly charged ions and # indicates an unidentified peak at m/z=2001.0 and 2744.4 daltons.

Figure 2C:
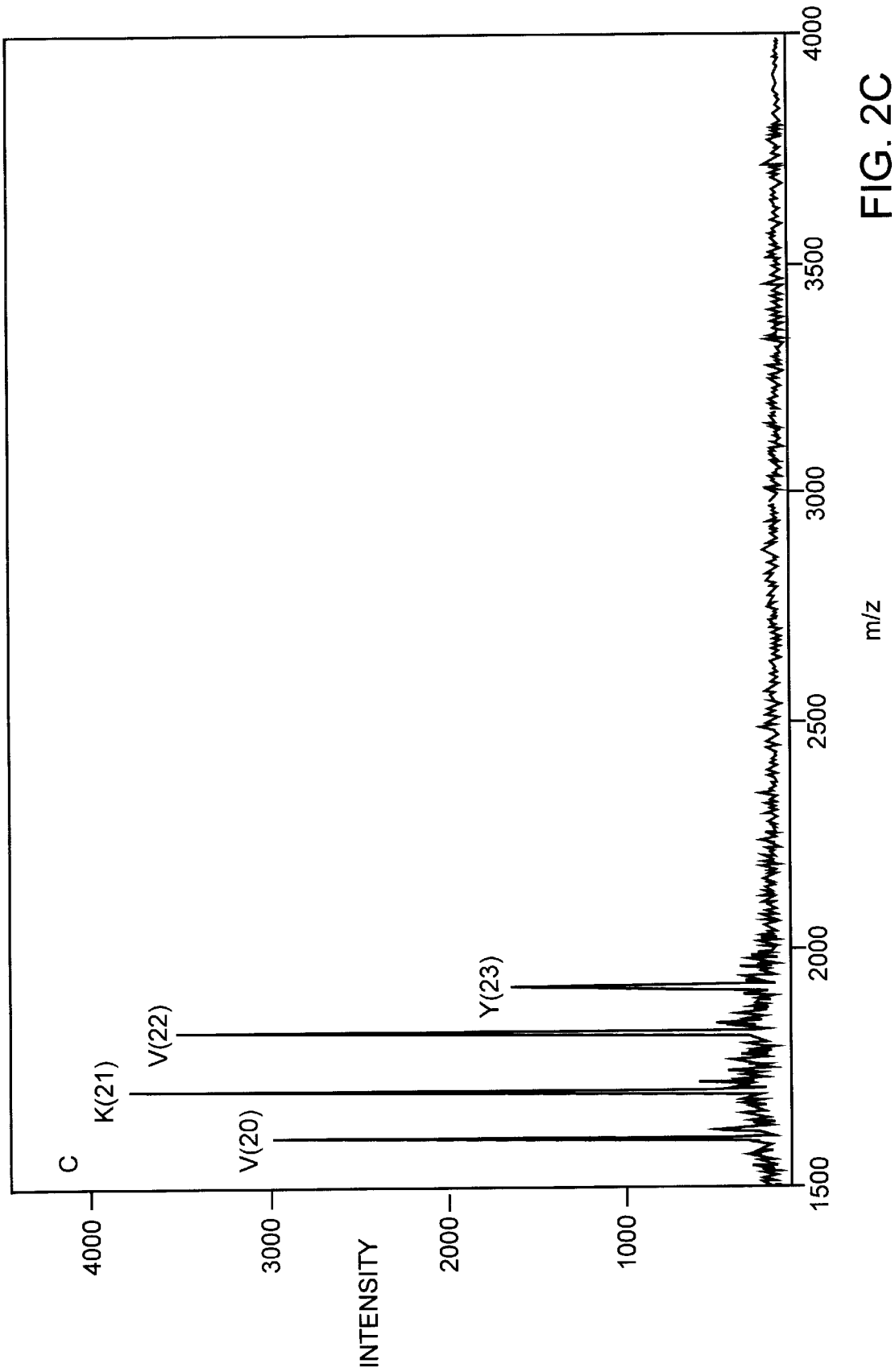

The lack of phase control of the enzymatic digestion creates the peptide ladders that are observed in this figure. After 1 min of digestion (FIG. 2A), 9 detectable peptide populations exist including the intact ACTH 7-38 fragment and peptides representing the loss of the first 8 amino acids from the C-terminus. The 5 min aliquot (FIG. 2B) shows that the peptide populations representing the loss of Ala(32) and Ser(31) have become much more predominant than the 1 min aliquot. Amino acid losses of 11 residues, Ala(32) through Val(22), are present at this digestion time. FIG. 2C shows the final detected amino acids of Lys(21) and Val(20) as 4 major peptide populations are detected. Upon increasing the enzyme concentration 2-fold at 25 min, no further digestion was observed through 24 h. The digestion proceeded through the Val(20) and stopped at the amino acid run of peptide-LysLysArgArgPro (residues 9–13 of SEQ ID NO:22). Although CPY may proceed rapidly through proline (e.g., Pro(24)), the basic residue, arginine, at the penultimate position in this case proved to be a combination refractory to CPY.

The lack of phase control coupled with the varied rates of hydrolysis poses problems unique to enzymatic sequencing. Varying ion intensities for the peaks in FIG. 2 are due primarily to the rates of hydrolysis that vary according to the amino acids at the C-terminus and penultimate position. When a residue is hydrolyzed at a low rate compared to the neighboring residues, the concentration and, therefore, signal of the peptide population representing the loss of that residue will be small relative to that of the preceding amino acid. This is seen in the mass spectra given in FIG. 2. The cleavage of Ala(34) is shown to be slow resulting in the large signal representing the loss of Phe(35). The hydrolysis of glycine and valine are also shown to be slow as the peaks representing the loss of Ala(27) and Tyr(23) are comparatively more intense than those of Gly(26) and Val(22), respectively.

The prior-art time-dependent method presented herein is the result of extensive method optimization and is optimized for obtaining the maximum sequence information in the shortest amount of time. For this particular optimized case, detectable amounts of all populations were observed over 25 min in the three selected time aliquots. This was not the case for numerous preliminary solution-phase digestions that were performed during the method optimization that led to the choice of these optimized conditions. At higher concentrations of CPY the peaks representing the loss of Glu(28) and Pro(24) were often not observed, indicating that CPY cleaves these residues very readily when alanine and tyrosine are at the penultimate positions, respectively. Lower concentrations of CPY allowed for all amino acids to be sequenced but often required long periods of time, e.g., days, for sufficient digestion. In the instance disclosed herein, an enzyme-to-substrate ratio of $1.67 \times 10^8$ units CPY/mole peptide was finally found to offer sufficient sequence information in 25 min of digestion.

Figure 3:
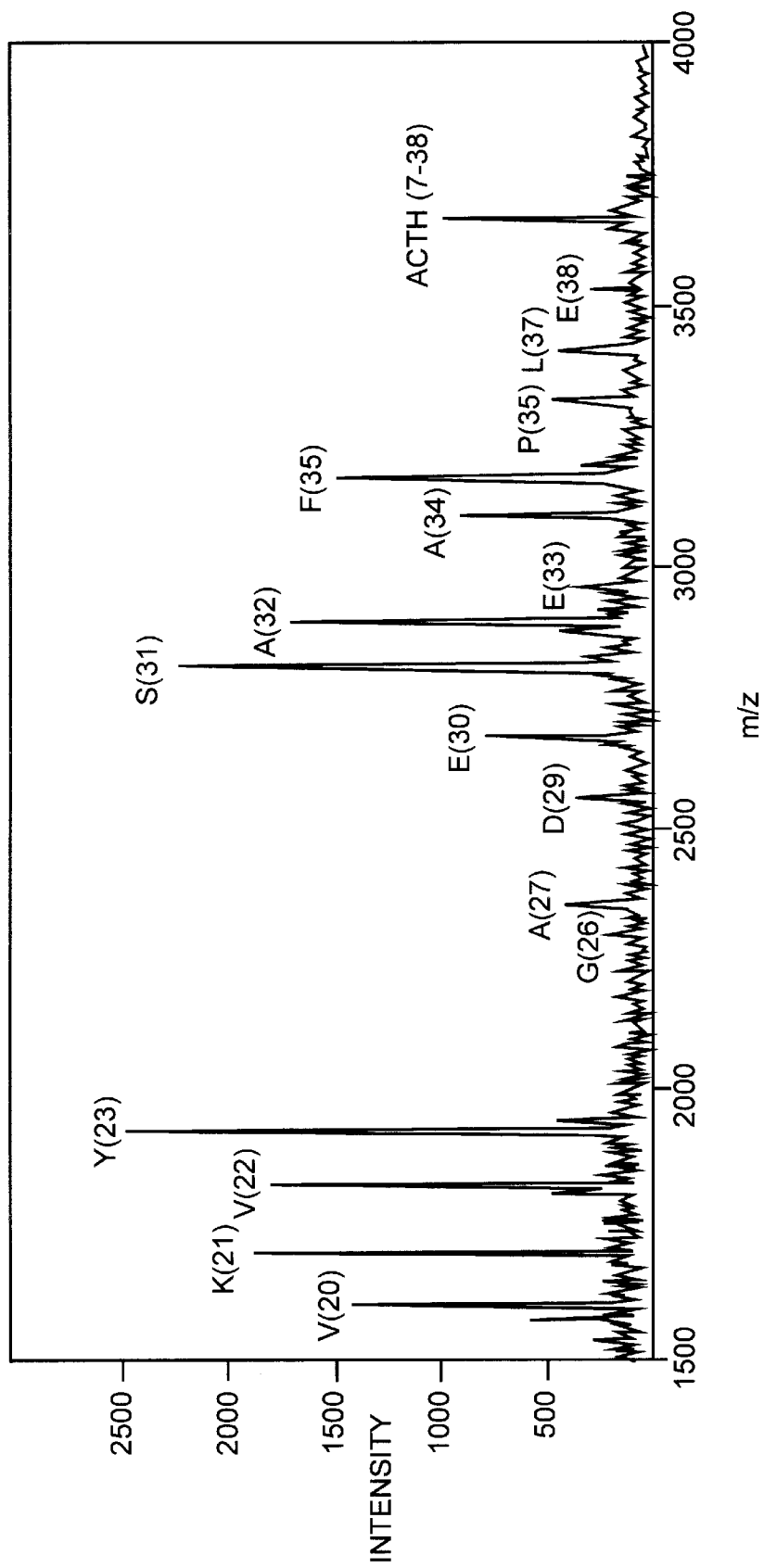
FIG. 3 is a MALDI mass spectra resulting from the pooling of the 15 s, 105 s, 6 min and 25 min quenched aliquots.

Alternatively, upon pooling aliquots from 15 s, 105 s, 6 min, and 25 min of total reaction time, MALDI analysis shows that a peptide ladder is formed that contains peaks that represent the loss of almost all amino acids from the C-terminus (FIG. 3). All amino acid losses are observed except for those of Glu(28), Asn(25), and Pro(24) which were present as small peaks in the 6 min aliquot and subsequently diluted to undetectable concentrations in this pooled fraction.

A sequence gap is observed here as the peptide populations representing the loss of Glu(28), Asn(25) and Pro(24) exist below a signal-to-noise ratio of 3. These populations were observed as small peaks in the 6 min aliquot mass spectrum but, upon the 4-fold dilution with the other aliquots, exist in too small a concentration to be detected. This emphasizes the necessity of recording individual mass spectra for each time aliquot. The less time-demanding procedure of recording a single spectrum representing pooled results not only created sequence gaps, but lost the time-dependent history of the digestion.

As illustrated above, solution-phase digestion suffers from a number of disadvantages. A large amount of time, enzyme and peptide is required for method optimization in order to obtain significant digestion in a short amount of time while preserving all possible sequence information. For each peptide from which sequence information is to be derived, some time-consuming method development must be performed since a set of optimum conditions for one peptide is not likely to be useful for another peptide given the composition dependent hydrolysis rates of CPY. An alternative strategy is to perform the concentration-dependent hydrolysis on the MALDI sample surface as described below.

(b) On-Plate Sequencing:

FIG. 1 depicts a VOYAGER™ sample plate for MALDI analysis comprised of a 10×10 matrix of 1 $\mu$L wells etched into the stainless steel base. These wells serve as microreaction vessels in which on-plate digestions may be performed. The physical dimensions of the plate are 57×57 mm and the wells are 2.54 mm in diameter.

Half-$\mu$L amounts of both enzyme and substrate were placed in a well and mixed with the pipet tip. The digestion continued for about 10 min until solvent evaporation terminates the reaction. At this time, the digestion mixture was resuspended by placing 1 $\mu$L of the matrix in the well. Since the CHCA matrix is solubilized in 1:1 ACN:0.1% TFA, both hydrophilic and hydrophobic peptide populations from the digest mixture should be resuspended with the low pH prohibiting any further CPY activity. The matrix crystal formation does not appear to be altered (as compared to the time-course experiment) by performing the digestion on-plate. This on-plate strategy significantly decreased the method optimization time by allowing multiple concentration-dependent (time-dependent) digestions to be performed in parallel. Also, sample losses upon transfer(s) from reaction vial to analysis plate were circumvented using the on-plate approach as all digested material is available for mass measurement.

Figure 4B:
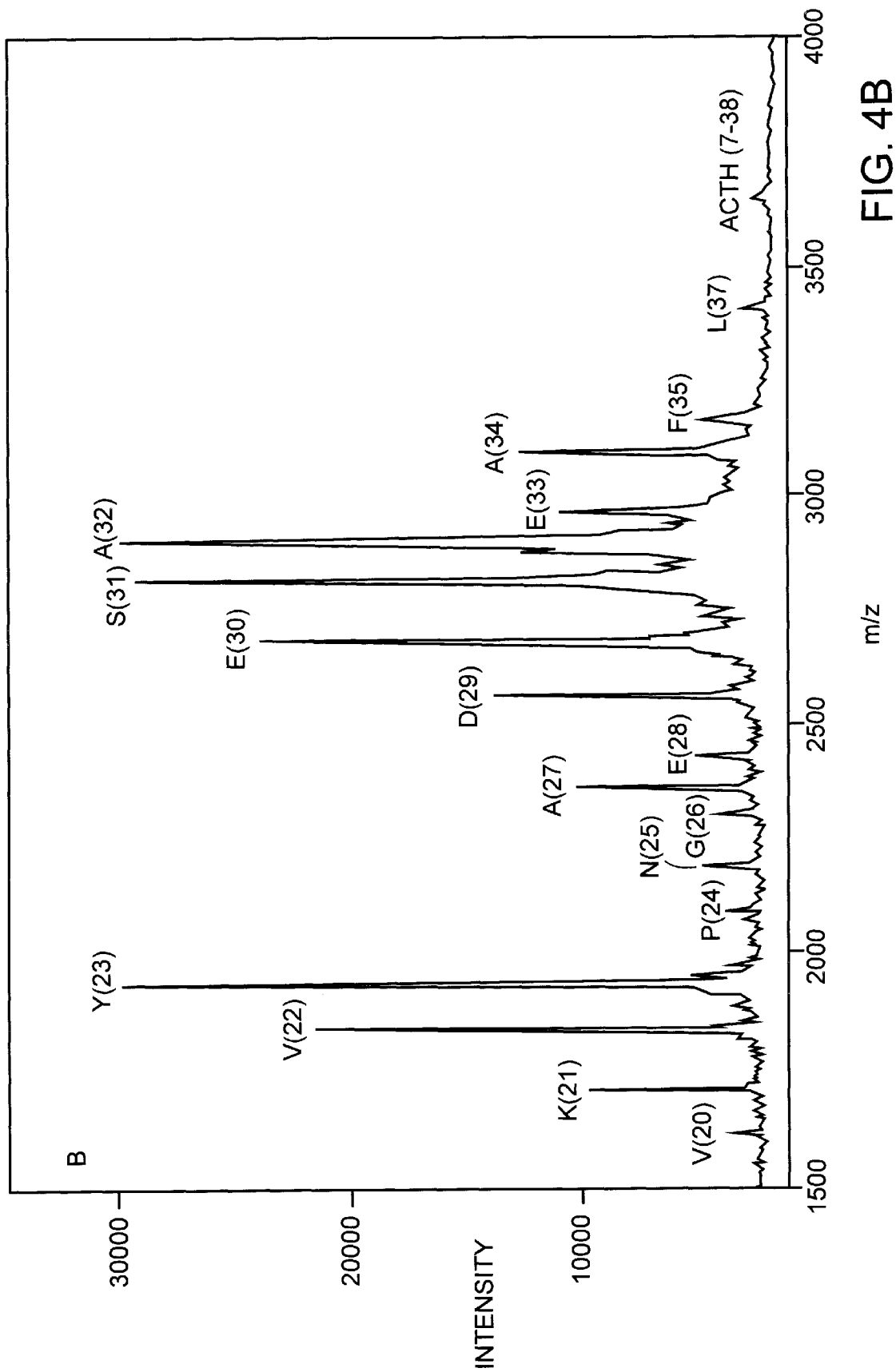

MALDI spectra corresponding to the on-plate concentration dependent digestions of the ACTH 7-38 fragment for CPY concentrations of $6.10 \times 10^{-4}$, and $1.53 \times 1^{-3}$ units/$\mu$L, respectively, are illustrated in panels A and B of FIG. 4. Panel A and B show the spectra obtained from digests using CPY concentrations of $6.10 \times 10^{-4}$ and $1.53 \times 10^{-3}$ units/$\mu$L, respectively. Laser powers significantly above threshold were used to improve the signal-to-noise ratio of the smaller peaks in the spectrum at the expense of peak resolution. The symbol * indicates doubly charged ions and # indicates an unidentified peak at m/z-2517.6 daltons.

The lower concentration digestion yielded 12 significant peaks representing the loss of 11 amino acids from the C-terminus. The digestion from the higher concentration of CPY showed some overlap of the peptide populations present at the lower concentration as well as peptide populations representing the loss of amino acids through the Val(20). The concentration of the peptides representing the loss of the first few amino acids have decreased to undetectable levels (approximately <10 fmol) with the exception of the Leu(37) peak. By integrating the information in both panels, the ACTH 7-38 fragment sequence can be read 19 amino acids from the C-terminus without gaps, stopping at the same amino acid run of peptide-Lys Arg Arg Pro (residues 9–13 of SEQ ID NO:22) as the time-dependent digestion. FIG. 4 represents 2 of the 9 CPY concentrations that were performed simultaneously. The method optimization, in this case, was inherent in the strategy. The total time of method development (optimal digestion conditions), digestion, data collection and data analysis was under 30 min using this on-plate approach. The consumption of both peptide and enzyme was minimal as a total of 5 pmol of total peptide was digested across the 10 well row containing 9 digestions and 1 well with peptide plus water. Also, only 1.97 pmol of CPY (assuming 100 unit/mg and MW=61,000) was required for the entire experiment.

TABLE 1

| Peptide | SEQ ID Nos. | Sequence | Average Mass | Charge | Polarity |
|---|---|---|---|---|---|
| Sleep Inducing Peptide | 1 | TreAlaGlyGlyAspAlaSerGlyGlu | 848.8 | −2.0 | polar |
| Amino Terminal Region of Hbs β chain[3] | 2 | ValHisLeuTrpTyrProValGluLys | 922.1 | +0.5 | mid |
| Interleukin-1β 163–171 Fragment[3] | 3 | ValGlnGlyGluGluDerAsnAspLys | 1005.0 | −2.0 | polar |
| TRH Precursor | 4 | LysArgGlnShiProGlyLysArg | 1006.2 | +4.5 | very |
| Bradykinin | 5 | ArgProProGlyPheSerProPheArg | 1061.2 | +2.0 | mid |
| Lutenizing Hormone Releasing Hormone[3] | 6 | ProGluHisTrpSerTyrGlyLeuArsPheGly.amide | 1182.3 | +1.5 | mid |
| Physalaemin | 7 | pyroGluAlaAspProAsnLysPheTyrGlyMetLeu.amide | 1265.4 | 0 | mid |
| Angiotensin 1 | 8 | AspArgValTyrIleHisProPheHisLeu | 1295.5 | +1.0 | non |
| Renin Inhibitor | 9 | ProHisProPheHisPheValTyrLys | 1318.5 | +2.0 | non |
| Kassinin | 10 | AspValProLysSerAspGlnPheValGlyLeuMet.amide | 1334.5 | −2.0 | non |
| Substance P | 11 | ArgProLysProGlnGlnPheGlyLeuMet.amide | 1347.6 | +3.0 | mid |
| T-Antigen Homolog | 12 | CysGlyTyrGlyProLysLysArgLysValGlyGly | 1377.7 | +5.0 | polar |
| Osteocalcin 7–19 | 13 | GlyAlaProValProTyrProAspProLeuGluProAsp | 1407.6 | −1.0 | mid |
| Thymopoietin II 29–41 Fragment | 14 | AlaAspSerGlyGluGlyAspPheLeuAlaGluGlyGlyGlyValArg | 1536.6 | −3.0 | mid |
| Bombesin | 15 | GlyGlnArgLysAspValTyrValGlnLeuTyrLeu | 1610.8 | 0 | polar |
| ACTH 11–24 Fragment | 16 | pyroGluGlnArgLeuGlyAsnGlnTrp*AlaValGlyHis)LeuMet.amide | 1619.9 | +1.5 | mid |
| α-Melanocyte Stimulating Hormone | 17 | LysProValGlyLysLysArgArgProValLysValTyrPro | 1652.1 | +6.0 | mid |
| Angiotensinogen 1–14 Fragment | 18 | AspTyrSerThrSerMetGluAspPheArsTrpGlyLysProVal.amide | 1664.9 | +1.5 | mid |
| Angiogenin | 19 | AspArgValTyrIleHisProPheHisLeuLeuValTyrSer | 1759.0 | +1.0 | non |
| Glucagon | 20 | GluAsnGlyLeuProValHisLeuAspGlnSerIle(PheArgArs | 1781.0 | +0.5 | mid |
| ACTH 7–38 Fragment | 21 | HisSerGlnGlyThrPheThrSerAspTyrSerLysTyrLeuAspSerArgArgAlaGlnAspPheValGlnTrp(LeuMetAsn)Thr | 3482.8 | +1.0 | polar |
| | 22 | PheArgTrpGlyLysProValGlyLysLysArgArgProValLysValTyrProAsnGlyAlaGluAlaGluAlaPheProLeuGlu | 3659.15 | +2.0 | polar |

[1] calculated
[2] at pH 6.5
[3] no sequence information was obtained

Listed in Table 1 are the peptides that have been digested and analyzed using this novel on-plate strategy. These peptides were selected to represent peptides of varying amino acid composition, size (up to MW=3659.15), charge and polarity. The bolded amino acids indicate that a peak representing the loss of that residue was observed in one or more of the MALDI spectra taken across the row of digestions. In order to be able to identify a residue, the peak representing the loss of that amino acid and the preceding amino acid must be present. The residues that are enclosed in parenthesis are those for which the sequence order could not be deduced. Overall, CPY offered some sequence information from the C-terminus for most of the peptides digested, lending no sequence information in only three of the 22 cases. In two of these three cases, the C-terminus was a lysine followed by an acidic residue at the penultimate position. CPY has been reported to possess reduced activity towards basic residues at the C-terminus, and the presence of the neighboring acidic residue seems to further reduce its activity. In the case of the lutenizing hormone releasing hormone (LH-RH), the C-terminal amidated glycine followed by proline at the penultimate position inhibited CPY activity which agrees with reports of CPY slowing at both proline and glycine residues (Hayashi et al. (1975) *J. Biochem.* 77:69–79; Hayashi, R. (1976) *Methods Enzymol.* 45:568–587). CPY is known to hydrolyze amidated C-terminal residues of dipeptides and is shown here to cleave those of physalaemin, kassinin, subtance P, bomesin, and α-MSH.

As illustrated by the data in Table 1, CPY was able to derive sequence information from all of the peptides, except LH-RH, that possess blocked N-terminal residues (physalaemin, bombesin and α-MSH). This is significant as these peptides would lend no information to the Edman approach. A number of the peptides were sequenced until the detection of the truncated peptide peaks were impaired by the presence of CHCA matrix ions (<600 daltons). The sequencing of the other peptides did not go as far as a combination of residues at the C-terminus and penultimate position that inhibited CPY activity were encountered. Bombesin, angiogenin and glucagon gave gaps in the sequence as residues that were cleaved slowly were followed by residues hydrolyzed more rapidly, as discussed above. The feasibility of the on-plate CPY digestion/MALDI detection strategy appeared to be independent of the overall polarity and charge of the peptide.

Figure 5A:
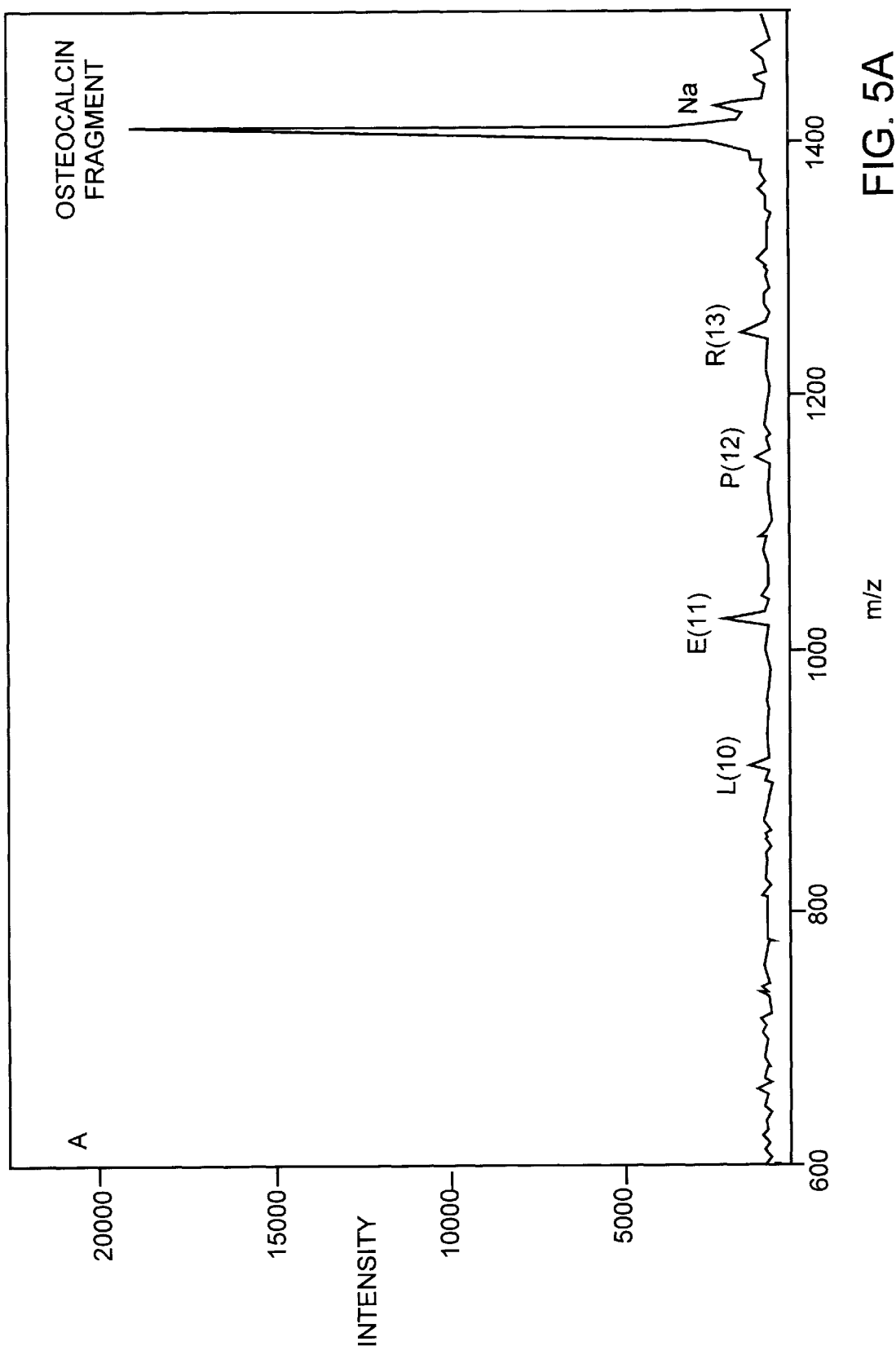
FIG. 5 is a MALDI spectra of three selected peptides, osteocalcin 7-19 fragment [Gly Ala Pro Val Pro Tyr Pro Asp Pro Leu Glu Pro Arg] (SEQ. ID. NO:13) (A) angiotensin 1 [Asp Arg Val Tyr Ile His Pro Phe His Leu ] (SEQ ID No:(B) and bradykinin [Ang Pro Pro Gly Phe Ser Pro Phe Arg] (SEQ. ID NO.5) (C).
Figure 6A:
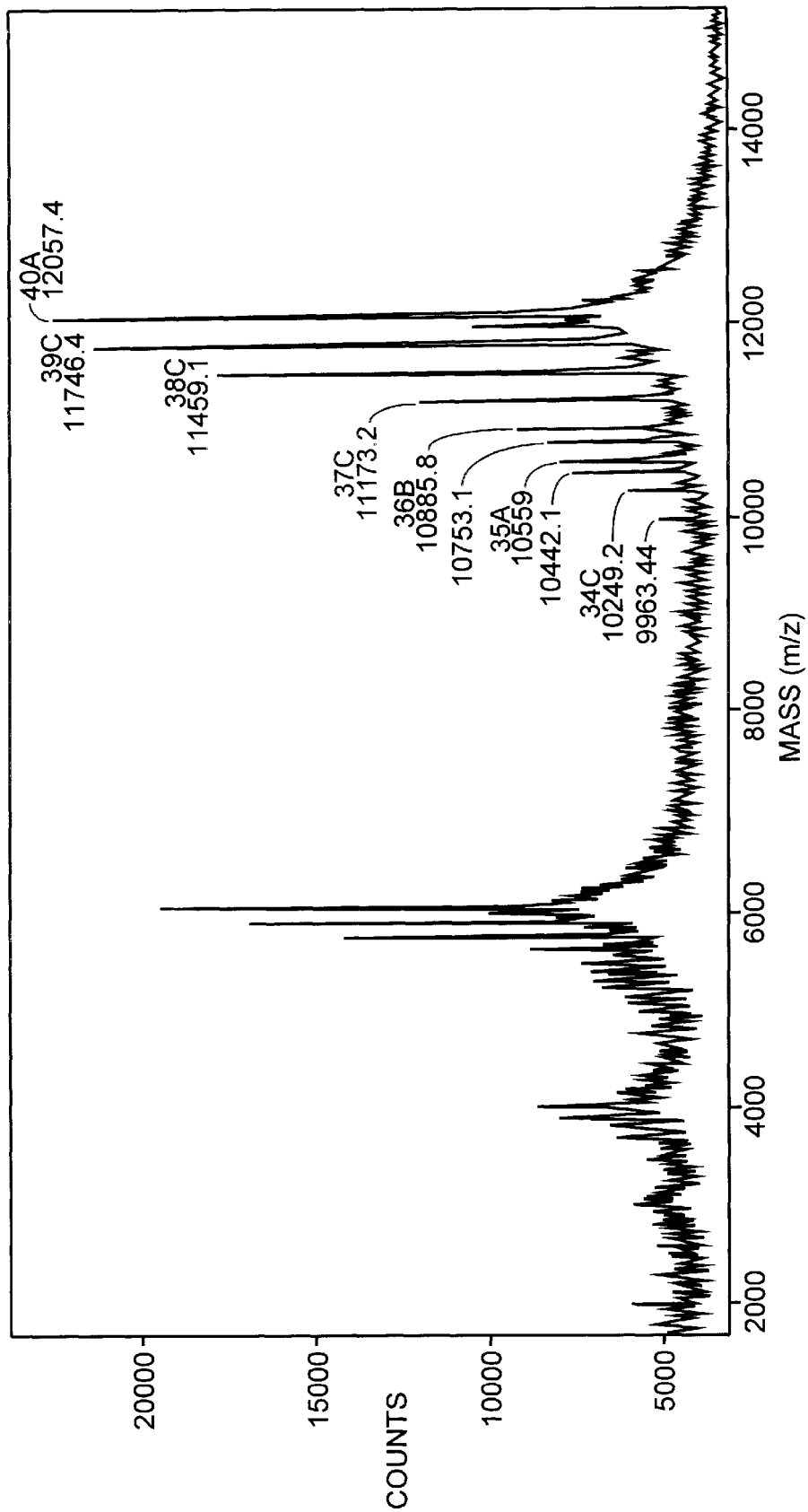
FIG. 6A–6E are various MALDI spectra of exonuclease hydrolysis of nucleic acid polymer.
Figure 6B:
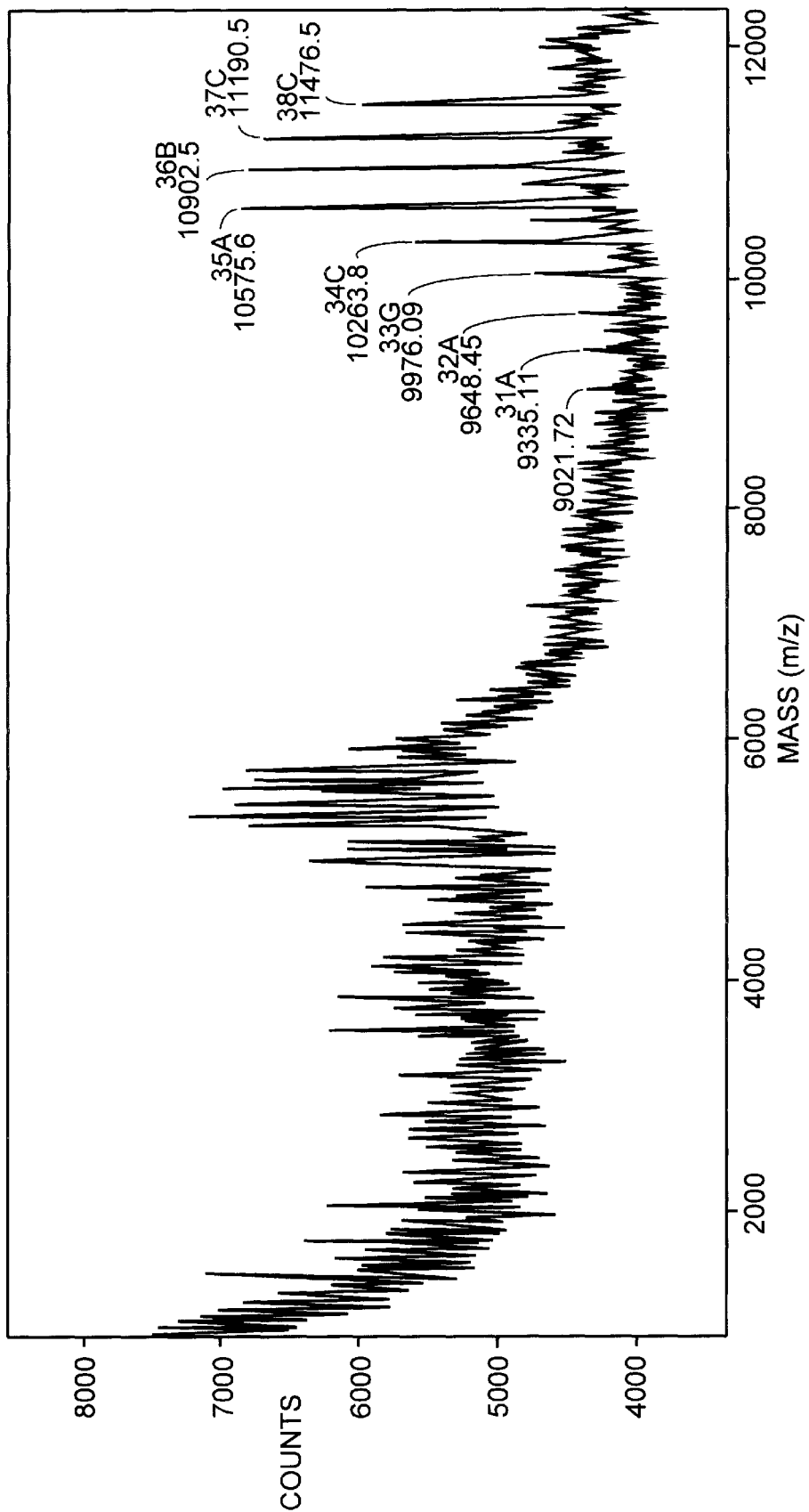
Figure 6C:
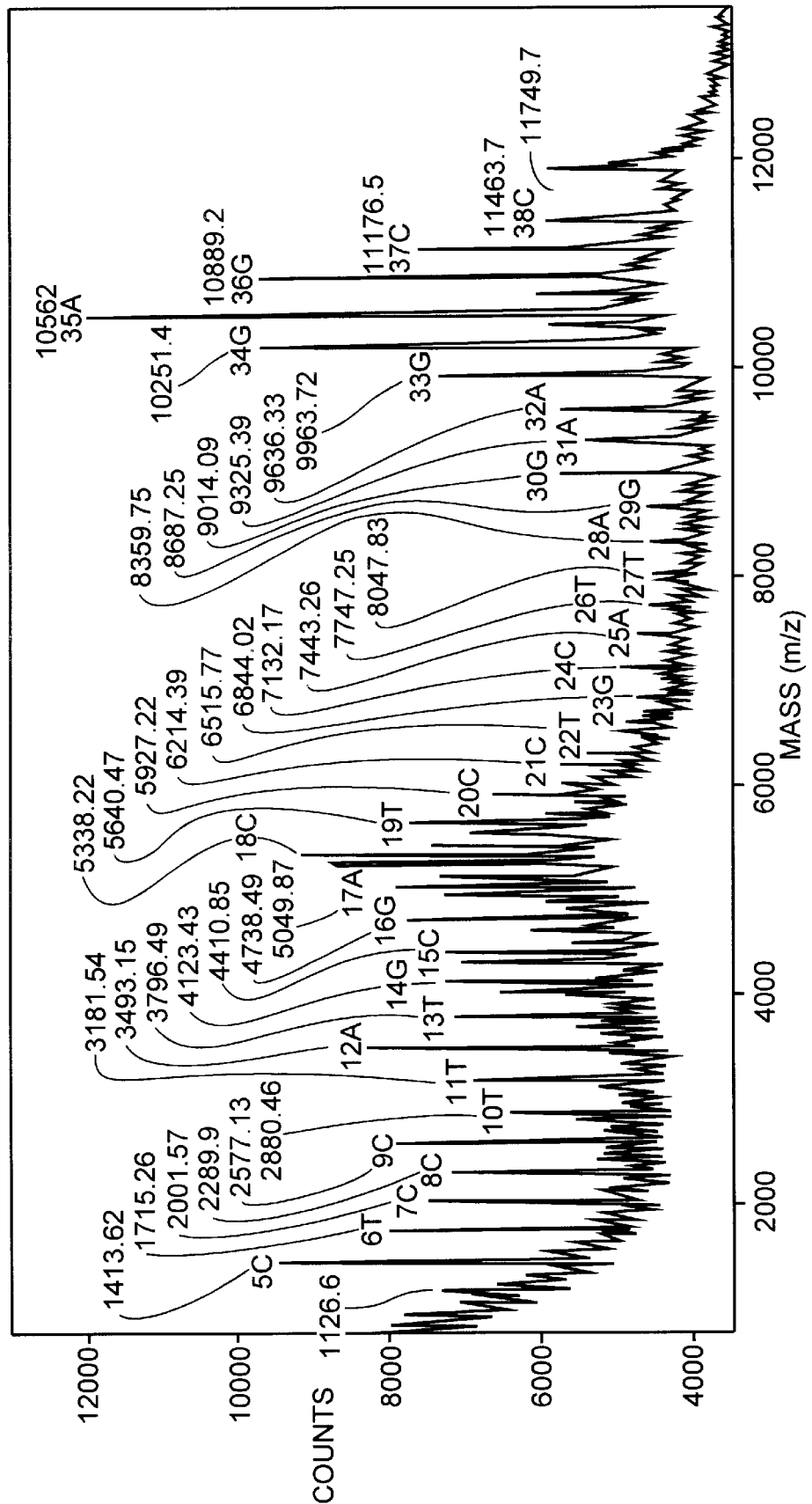
Figure 6D:
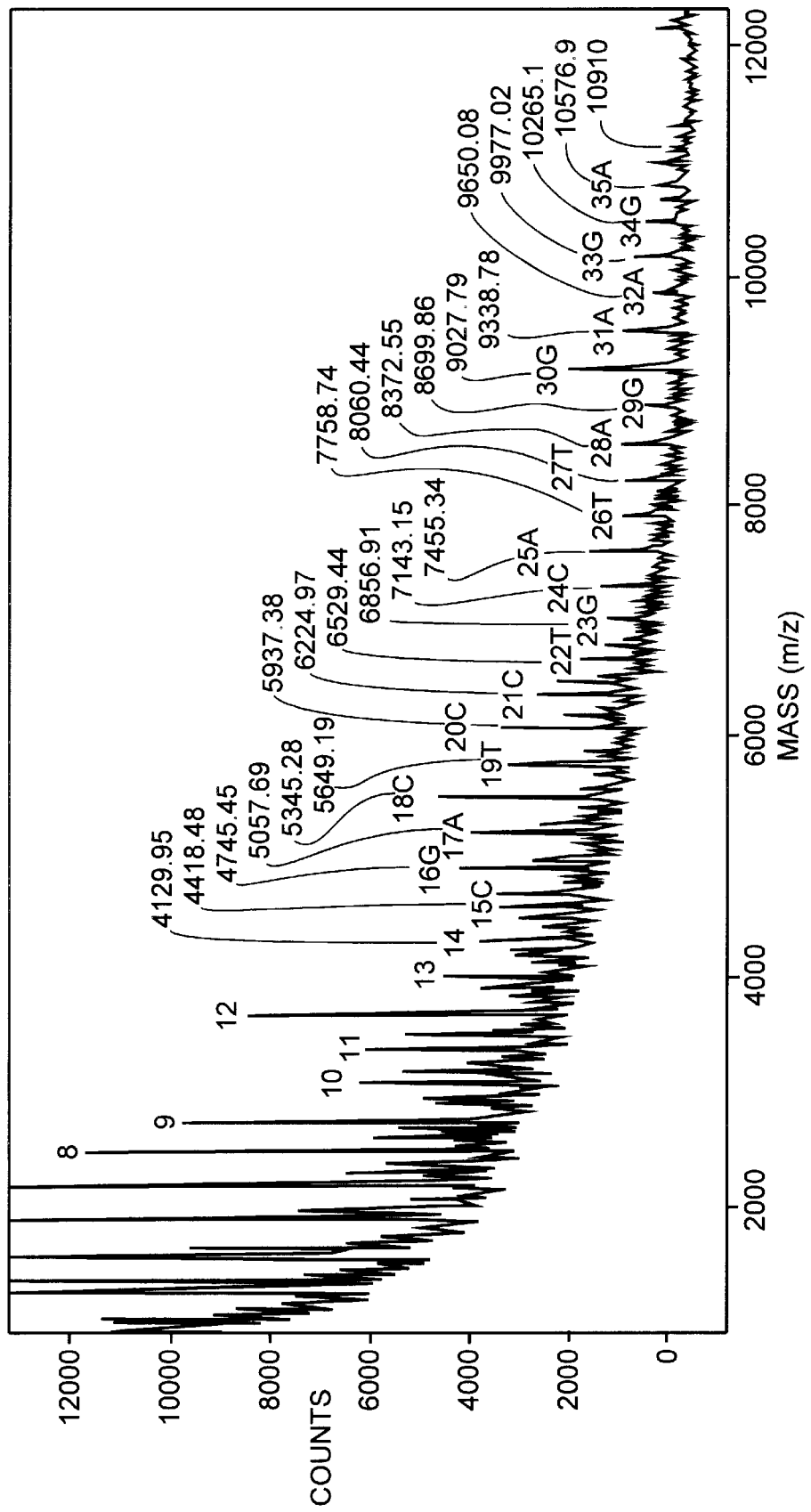
Figure 6E:
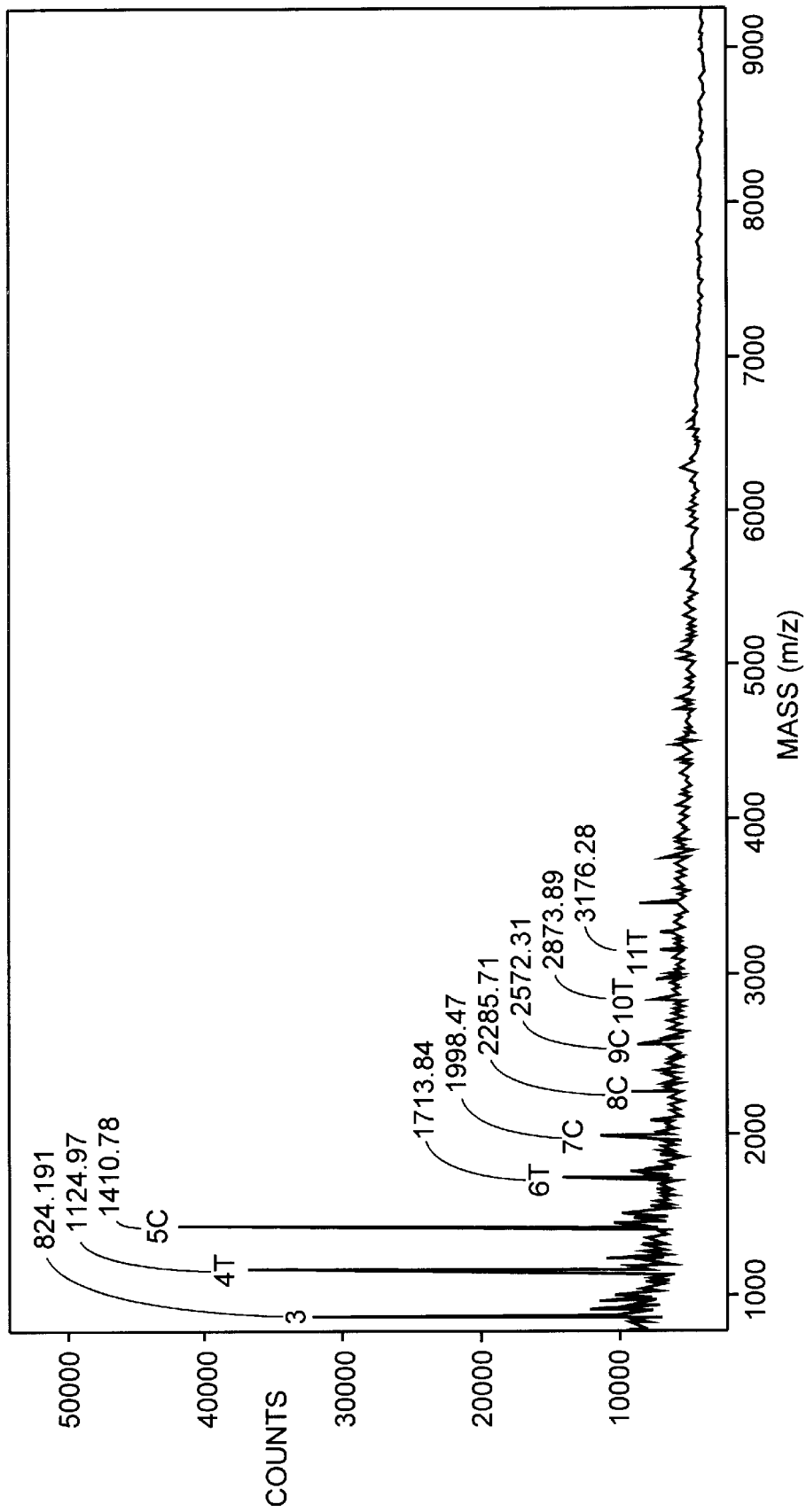

FIG. 5 shows selected on-plate digestions of osteocalin 7-19 fragment, angiotensin 1 and bradykinin resulting from on-plate digestions using CPY concentrations of $3.05 \times 10^{-3}$, $3.05 \times 10-4$, and $6.10 \times 10^{-4}$ units/$\mu$L, respectively. The symbol Na denotes a sodium adduct peak and # denotes a matrix peak at m/z-568.5 daltons.

Each spectrum represents the results of one of the 9 digestions that was performed across the row of wells. In the case of the osteocalcin 7-19 fragment, CPY can proceed through proline (Martin, B. (1977) *Carlsburg Res. Commun.* 42:99–102; Breddam et al. (1987) *Carlsburg Res. Commun.* 52:55–63; Breddam, K. (1986), *Carlsburg Res. Commun.* 51:83–128; Hayashi, R. (1977) *Methods Enzymol.* 74:84–94; Hayashi et al. (1973) *J. Biolog. Chem.* 248:2296–2302); the presence of Asp and His at the respective penultimate positions of the two peptides prohibited further CPY activity. Bradykinin is shown to sequence until the matrix begins to interfere with peak detection. For all three of the selected peptides, the total sequence information obtained for the overall 9 well digestion is represented in the single digestion shown. For many other peptides this was not the case. The total sequence information is often derived from 2 or more of the wells as is the case with ACTH 7-38 fragment given in FIG. 4.

Example 3. Statistical Analysis of Ladder Sequencing by Maldi (a) General Principles of Statistical Analysis According to the Instant Invention As disclosed above, once the truncated ladders have been formed, matrix is added to the well and multiple measurements were taken from the wells in which peaks representing the loss of an amino acid(s) are present. Statistical interpretation involving the use of t-statistics then allowed assignments to be made with an associated confidence interval. The two-tailed test for one experimental mean, $$t_{calculated} = \frac{|\bar{x} - \mu| \sqrt{N}}{S}$$

where $\bar{x}$ is the experimental mean mass difference, $\mu$ is the asserted mass difference, N is the number of replicates performed, and S is the experimental standard deviation of the mean, was applied. All conceivable masses (single residue, di-residue, tni-residue, etc., as well as modified residue masses) were used as $\mu$, the asserted mass, to generate a list of $t_{calculated}$ values that were then compared against tabulated values for given confidence intervals. All masses that did not statistically differ from the asserted mass, $t_{calculated} < t_{table}$, were statistically assigned to that residue(s) at the given level of confidence. This information was used to check hypothesized composition or used to search a database for a sequence. When performing database searching, these levels of confidence can be used in the search algorithm as a tool to aid in obtaining quality "hits."

Additionally, the interpretation of data utilized an automated process of acquiring and interpreting the data using software feedback control. The data interpretation software controls the number of acquisitions (minimum of 2) that are required to statistically differentiate multiple candidates for an amino acid assignment. The operator has control of specifying to what minimum statistical level of confidence the assignment(s) should meet.

(b) Analysis of Experimentally-Obtained Mass-to-Charge Ratio Data: Peptides

The use of MALDI for the analysis of truncated ladders as disclosed herein is critical for obtaining accurate sequence data. In the prior art, the technique has been used almost exclusively to sequence peptides of a defined sequence for which the mass accuracy of the measurement is of little importance. In contrast, the methods disclosed herein are useful for the sequence determination of peptides of unknown sequence. By comparing known molecular masses to the MALDI derived masses for only a few mass measurements, artisans previously have made only general statements of instrumental mass accuracy (e.g., better than 0.1%), but, ascribing this mass accuracy to any individual mass measurement for the purpose of residue assignment holds no statistical validity. Therefore, true residue assignment and direct application to unknowns has heretofore been both difficult and tentative. In order to derive amino acid sequences by ladder sequencing/MALDI strategies, statistical levels of confidence must be placed on residue assignments as disclosed herein.

To place confidence levels on residue assignments, the nature of the experimental errors first must be defined. For systems in which the errors are random, simple t-statistics can be used for amino acid assignment.

To assess the nature of the errors that dominate MALDI analysis of the above-described truncated peptide ladders, the Δ mass differences (i.e., experimental mass difference—actual amino acid mass) for all amino acid assignments made in the 15 aliquots (one spectrum per aliquot) removed from the time-dependent digestion of ACTH 7-38 fragment described above were measured to yield a gaussian distribution with a mean of 0.0089±0.605 (n=107). For this experiment $t_{calculated}$ (0.152)<$t_{table}$ (1.99) indicating that the null hypothesis that the average Δ mass difference=0 cannot be rejected at a 95% confidence level. This indicates that the error is random with no statistically significant systematic error. This is expected as any systematic errors that are present in the mass assignment of individual peptide peaks such as incorrect y-intercept values for two-point mass calibration should cancel out when calculating the mass difference of two adjacent peaks. There are possible systematic components of error that would not be canceled such as incorrect computation of the mass center of one of a set of two adjacent peaks due to partial resolution of the isotopes. This phenomenon was circumvented by the use of a smoothing filter such that all peaks were detected at the actual average mass values.

TABLE 2

| Amino Acid (position) | Actual Mass[1] | Experimental Mass[1,2] | Replicates |
|---|---|---|---|
| val (20) | 99.13 | 98.97 ± 0.52 (1.29) | 3 |
| lys (21) | 128.17 | 128.15 ± 0.48 (0.44) | 7 |
| val (22) | 99.13 | 99.20 ± 0.35 (0.27) | 9 |
| tyr (23) | 163.17 | 162.43 ± 0.11 (0.99) | 2 |
| pro (24) | 97.12 | 97.49 ± 0.14 (1.25) | 2 |
| asn (25) | 114.10 | 114.21 ± 0.82 (0.69) | 8 |
| gly (26) | 57.05 | 57.22 ± 0.88 (0.68) | 9 |
| ala (27) | 71.07 | 70.19 ± 0.49 (4.40) | 2 |
| glu (28) | 129.12 | 130.22 ± 0.47 (4.22) | 2 |
| asp (29) | 115.09 | 114.81 ± 0.58 (0.41) | 10 |
| glu (30) | 129.12 | 129.27 ± 0.61 (0.39) | 12 |
| ser (31) | 87.08 | 87.14 ± 0.47 (0.30) | 12 |
| ala (32) | 71.07 | 80.94 ± 0.49 (0.51) | 6 |
| glu (33) | 129.12 | 129.39 ± 0.42 (0.44) | 6 |
| ala (34) | 71.07 | 71.09 ± 0.30 (0.28) | 7 |
| phe (35) | 147.18 | 147.03 ± .73 (0.77) | 6 |
| pro (36) | 97.12 | 96.83 ± 0.64 (1.18) | 4 |
| leu (37) | 113.16 | 113.63 ± 0.54 (1.34) | 3 |
| glu (38) | 129.12 | 128.40 ± 0.52 (1.29) | 3 |

[1] the masses given are average means and in units of daltons
[2] the uncertainties of the experimental mass measurements are given as standard deviations (those in the parenthesis are 95% confidence intervals of the mean)

Table 2 represents a comparison of the actual average masses of the sequenced residues of the ACTH 7-38 fragment and the experimental mass differences with associated standard deviations and 95% confidence intervals calculated for the time-dependent digestion. The number of replicates indicate the number of spectra that possessed the detectable adjacent peaks required for the mass difference measurement of that particular residue. The need for a significant number of measurements in order to estimate the mean is obvious from the table as the 95% confidence level decreases as the square root of the number of measurements. For all of the residues sequenced, the actual mass fell within ±3 σ the experimental mass distribution. Calculated t-values for each case were less than the tabulated t-value for the 95% confidence interval signifying that the experimental mass is not significantly different than the actual known mass. In order to statistically assign the residues, a calculated t-value for each possible amino acid must be compared with the tabulated value. In other words, the actual masses of all possible amino acids must be used as an asserted mean, $\mu$, and each null hypothesis (i.e., $\bar{x}-\mu=0$) made such that a calculated t-value for each possible assignment can be compared to the tabulated value.

Assuming that only the 20 common unmodified amino acids are possible, this was done for the prior art time-dependent ACTH 7-38 fragment digestion. A summary of the results is given in Table 3. The bolded values are those which the experimental mean did not significantly differ from the asserted amino acid mean. Again, the need for adequate population sampling is apparent. There were only two measurements observed for the Glu(28) thereby resulting in a 95% confidence interval of 4.22 daltons (Table 2). This translates into an inability to distinguish between Gln, Lys, Glu and Met (Table 3). The 12 trials that were observed for Glu(30) gave a 95% confidence interval of 0.39 daltons, thereby rendering the Gln, Lys and Met statistically improbable amino acid assignments.

Table 3 represents calculated t-values for 19 sequenced amino acid experimental means in the ACTH 7-38 fragment given the asserted means of 20 common unmodified amino acids. The $t_{table}$ value is given at the end of each column. A $t_{calculated}<t_{table}$ indicates that the experimental mean is not significantly different that the mean of the asserted amino acid at 95% confidence interval. Each $t_{calculated}$ for which this is the case is indicated in bold.

TABLE 3

| | ACTH 7-38 Fragment Amino Acid Position | | | | | | | | | | | | | | | | | | |
|---|---|---|---|---|---|---|---|---|---|---|---|---|---|---|---|---|---|---|---|
| | 20 | 21 | 22 | 23 | 24 | 25 | 26 | 27 | 28 | 29 | 30 | 31 | 32 | 33 | 34 | 35 | 36 | 37 | 38 |
| Gly | | | | | | | 0.58 | 37.9 | | | | | 69.4 | | 123 | | | | |
| Ala | | | | | | | 47.2 | 2.54 | | | | 118 | 0.65 | | 0.18 | | | | |
| Ser | | | | | 105 | | | 48.7 | | | | 0.44 | 80.7 | | 141 | | 30.5 | | |
| Pro | 6.16 | | 17.8 | | 3.74 | | | | | | | 73.6 | | | | | 0.91 | | |
| Val | 0.53 | | 0.60 | | 16.6 | | | | | | | | | | | | 7.19 | | |
| Thr | 7.09 | | 16.3 | | | | | | | | | | | | | | | | |
| Cys | | | | | | | | | | | | | | | | | | 33.6 | |
| Leu/Ile | | | | | 3.62 | | | | | | | | | | | | | 1.51 | |
| Asn | | | | | 0.38 | | | | | 3.87 | | | | | | | | 1.51 | |
| Asp | | 72.0 | | | 3.04 | | | | 45.5 | 1.53 | | | | | | | 4.68 | | 44.3 |
| Gln | | 0.11 | | | | | | | 6.29 | 72.6 | | | | | | | | | 0.90 |
| Lys | | 0.11 | | | | | | | 6.17 | | 6.25 | | | 7.12 | | | | | 0.77 |
| Glu | | 5.35 | | | | | | | 3.31 | | 0.85 | | | 1.57 | | | | | 2.40 |

TABLE 3-continued

| | ACTH 7–38 Fragment Amino Acid Position | | | | | | | | | | | | | | | | | | |
|---|---|---|---|---|---|---|---|---|---|---|---|---|---|---|---|---|---|---|---|
| | 20 | 21 | 22 | 23 | 24 | 25 | 26 | 27 | 28 | 29 | 30 | 31 | 32 | 33 | 34 | 35 | 36 | 37 | 38 |
| Met | | | | | | | | | 2.95 | | 11.0 | | | 10.6 | | | | | 9.33 |
| His | | | | | | | | | 20.8 | | | | | | | 33.2 | | | |
| Phe | | | | | | | | | | | | | | | | 0.50 | | | |
| Arg | | | | 80.4 | | | | | | | | | | | | 30.7 | | | |
| Tyr | | | | 9.64 | | | | | | | | | | | | | | | |
| Trp | | | | 305 | | | | | | | | | | | | | | | |
| t$_{table}$[1] | 4.30 | 2.45 | 2.31 | 12.7 | 12.7 | 2.37 | 2.31 | 12.7 | 12.7 | 2.26 | 2.20 | 2.20 | 2.57 | 2.57 | 2.45 | 2.57 | 3.18 | 4.30 | 4.30 |

[1] the tabulated t value associated with an area of 0.025 in one tail of the t-distribution corresponding to the appropriate degrees of freedom, $\nu$, where $\nu = n - 1$.

Table 4 summarizes the results of the statistical amino acid assignments for the 19 amino acids sequenced from the C-terminus of ACTH 7-38 fragment using the prior art time-dependent strategy. The masses of the listed amino acids could not be statistically differentiated from the experimentally derived mass difference at the given confidence levels. The amino acids indicated in bold are the known residues existing at the given positions. The confidence intervals indicated are the highest levels at which all amino acid masses other than those indicated are statistically different from the experimental mean.

TABLE 4

| ACTH 7–38 Fragment Amino Acid Position | Amino Acid Assignments[1] | Confidence Interval (c.i.) |
|---|---|---|
| 20 | Val | 95% < c.i < 98% |
| 21 | Gln/Lys | c.i. > 99.8% |
| 22 | Val | c.i > 99.8% |
| 23 | Tyr | 99% < c.i. < 99.8% |
| 24 | Pro | 95% < c.i. < 98% |
| 25 | Asn | 98% < c.i. < 99% |
| 26 | Gly | c.i. > 99.8% |
| 27 | Ala | 98% < c.i. < 99% |
| 28 | Gln/Lys/Glu/Met | 95% < c.i. < 98% |
| 28 | Met | 80% < c.i. < 90% |
| 29 | Asp | 99% < c.i. < 99.8% |
| 30 | Glu | c.i. > 99.8% |
| 31 | Ser | c.i. > 99.8% |
| 32 | Ala | c.i. > 99.8% |
| 33 | Glu | c.i. > 99.8% |
| 34 | Ala | c.i. > 99.8% |
| 35 | Phe | c.i. > 99.8% |
| 36 | Pro | 99% < c.i. < 99.8% |
| 37 | Leu(Ile)/Asn | 95% < c.i. < 98% |
| 38 | Gln/Lys/Glu | 98% < c.i. < 99% |
| 39 | Gln/Lys | 80% < c.i. < 90% |

[1] assuming that only the 20 common unmodified amino acids are probable candidates For example, the distinction between Gln and Lys for the amino acid assignment of residue 21 could not be made as the experimental mean (128.15 daltons) exactly bisected the asserted means of Gln (128.13 daltons) and Lys (128.17 daltons). The same phenomenon occurred in the assignment of residue 37. The experimental mean (113.63 daltons) bisected the asserted means of Leu(Ile) (113.16 daltons) and Asn (114.10 daltons). The assignments of the amino acids at positions 28 and 38 were difficult due to the small number of replicates taken (2 and 3, respectively). Residue 28 was assigned Gln/Lys/Glu/Met at a confidence interval greater than 95% but less than 98%. Table 3 shows that, for this residue, the asserted amino acid mass that resulted in the smallest $t_{calculated}$ was that of methionine. Using a confidence interval of 80%, the correct assignment of Glu is deemed statistically improbable. Likewise, the assignment of residue 38 was made as Gln/Lys/Glu at a confidence level of 95%, but the correct assignment (Glu) is again statistically improbable at an 80% level.

Since the errors are randomly distributed, all amino acids can be differentiated (except Leu and Ile) by sufficient population sampling. Approximating the experimental standard deviation to be that given above of s=0.604 for the overall experiment, it is approximated (using $t_{table}$=1.960) that >876 measurements would be required to differentiate Gln and Lys ($\Delta$ mass=0.04 daltons) at a 95% confidence interval. This number is experimentally impractical, but can be significantly lowered by reducing the standard deviation of the experimental mean. Decreasing the experimental standard deviation is of significant value as the number of samples required for the distinction between two amino acids to be made is proportional to the square of the experimental standard deviation of the mass difference. It is anticipated that mass shift reagents used to move peptide populations out of the interfering matrix are a possible chemical means for improving experimental error relating to peptides appearing in the low mass (<600 daltons) region. The use of reflectron and/or extended flight tube geometries are also expected to be instrumental methods suitable for reducing this error.

The protocol disclosed herein for statistical assignment of residues using the on-plate strategy involves multiple sampling from each well in which digestion is performed. The number of replicates required depends on the amino acid(s) that is(are) being sequenced at any one CPY concentration. For example, more replicates are required for mass differences around 113–115 daltons (Ile/Leu, Asn and Asp) and 128–129 daltons (Gln/Lys/Glu) than for mass differences around 163 (Tyr) or 57 (Gly) in order to be able to assure that all but one assignment are statistically unlikely. The experimental errors for this method appear to be as random (multiple replicates per sample) as for the timedependent digestion (one replicate per sample).

This general statistical protocol for residue assignment was applied to two adjacent peaks that represent the loss of two or more amino acids. In this case, the asserted means of all dipeptides, tripeptides, etc. can also be used to calculate t-values. The information concerning the order of the residues will be lost but the composition can be deduced. Using only single amino acid and dipeptide masses as asserted means this was done for angiogenin has a sequence gap of Phe—Arg (Table 1). The average experimental mass difference between the peaks representing the loss of Arg(15) and Phe(13) was 303.45±0.328 (n=5). For all single amino acid and dipeptide masses except Phe/Arg, the calculated t-values are greater than the tabulated t-value at a confidence interval of 99.8%. In this particular case, the identity of the amino acids that comprise the gap was determined, but their order remains experimentally unknown. This statistical strategy was also incorporated into a computer algorithm to perform interactive data analysis and interpretation of ladder sequencing/MALDI experiments.

Thus, as illustrated above, the use of CPY digestion coupled with MALDI detection as disclosed herein was effective for obtaining C-terminal sequence information. The ACTH 7-38 fragment yielded sequence information 19 amino acids from the C-terminus without gaps. The on-plate concentration-dependent approach was demonstrated as a useful method for performing multiple digestions in parallel which circumvented the need for time- and reagent-consuming method development. This on-plate strategy required less physical manipulations and less total amounts of enzyme and peptide. Of the 22 peptides attempted using the on-plate approach, all but three were successfully digested to yield some C-terminal sequence information. CPY was also shown to cleave amidated C-terminal residues, but possessed no activity towards certain combinations of residues existing at the C-terminus and penultimate position.

In summary, an integrated strategy for generating residue assignments from "on-plate" C- and N-terminal peptide ladder sequencing experiments was developed. This strategy is based on the logical combination of tasks involving:

1) the creation of peptide ladders from a concentration-dependent exopeptidase digestion strategy that utilizes the $\mu L$ -wells of the VOYAGER™ sample plate as microreaction vessels;
2) the use of the VOYAGER™ MALDI-TOF workstation as a tool to generate masses of the peptide fragment;
3) an interpretation algorithm based on t-statistics that allows elimination of asserted assignment candidates; and,
4) feedback control of the data acquisition software from the interpretation algorithm that governs the number of replicates that are acquired for the statistically-based assignments to be made completely or to a cost effective partial point.

(c) Analysis of Experimentally-Obtained Mass-to-Charge Ratio Data: Nucleic Acids The method disclosed herein has also been used to obtain sequence information about a nucleic acid polymer containing 40 bases. Hydrolysis using an exonuclease specific for the 3' terminus was conducted using different concentrations of Phos I (phosphodiesterase I) ranging from 0.002 $\mu U//\mu l$ to 0.05 $\mu U/\mu l$. Hydrolysis was allowed to proceed for 3 minutes. Spectra of hydrolyzed sequences using MALDI-TOF are depicted in FIGS. 6A–6E. Data integration as disclosed herein confirmed the sequence to be:

CGC TCT CCC TTA TGC GAC TCC TGC ATT AGG AAG CAG CCC A (SEQ ID NO.23).

Figure 7:
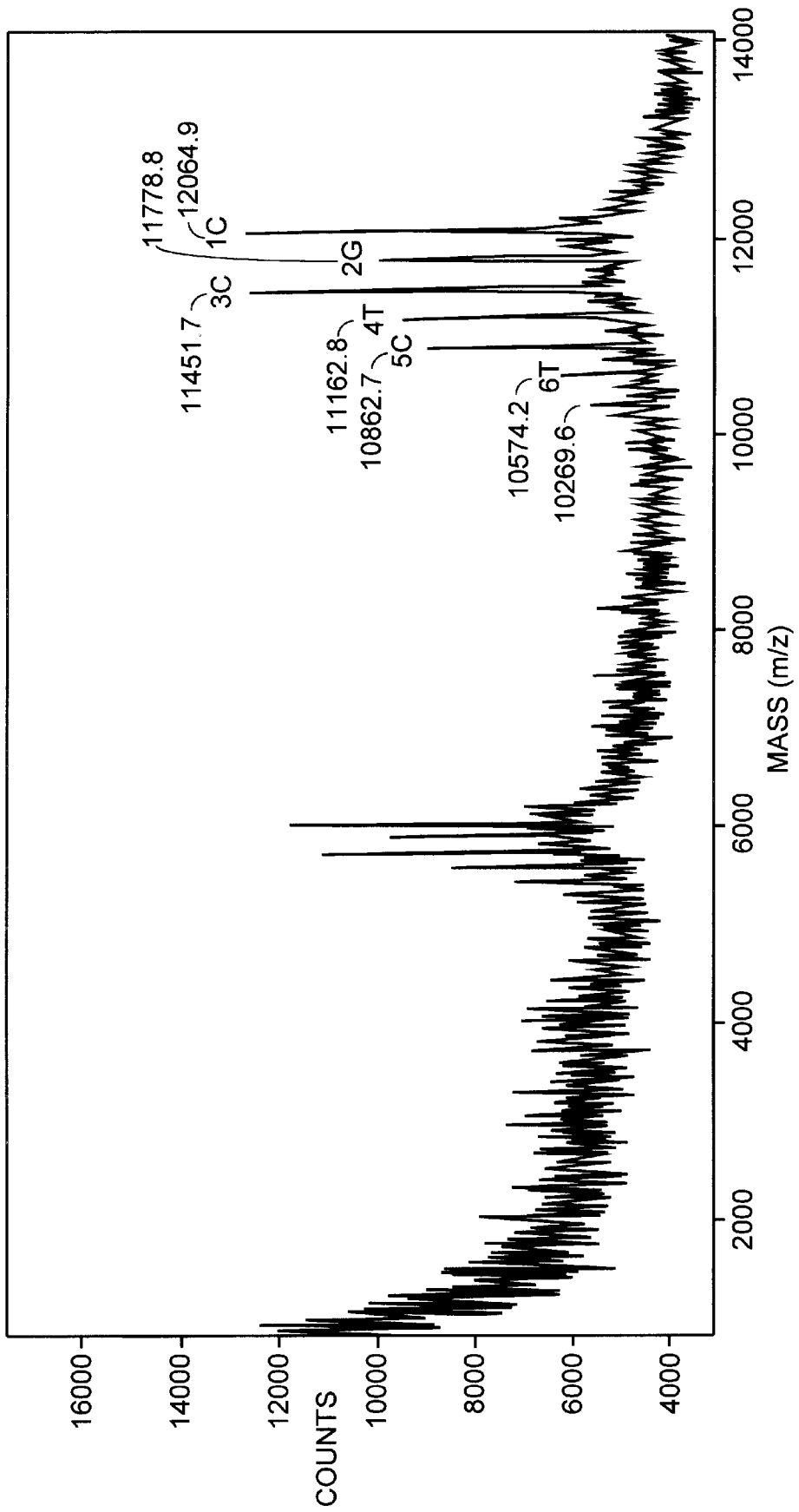
FIG. 7 is a MALDI spectrum of a hydrolyzed nucleic acid polymer combined with a light-absorbent matrix.

In a separate experiment, addition of a light-absorbent matrix CHCA was evaluated. A nucleic acid polymer containing 40 bases (as described above) was mixed with matrix and 0.4 $\mu U/\mu l$ of the exonuclease Phos II (phosphodiesterase II) which is specific for the 5' terminus. Hydrolysis in the presence of matrix was allowed to proceed for 10 minutes. The spectrum obtained by MALDI-TOF is depicted in FIG. 7. These data confirm the ability to combine polymer, hydrolyzing agent and matrix prior to mass spectrometry analysis. This reduces handling of reagents and facilitates sample processing. Using data similar to those in FIG. 7, the sequence of the nucleic acid polymer was confirmed to be as described above.

Example 4. Other Applications of the Instant Method

As disclosed herein, this strategy can be applied to the sequencing of any natural biopolymer such as proteins, peptides, nucleic acids, carbohydrates, etc. as well as synthetic biopolymers such as PNA and phosphothiolated nucleic acids. The ladders can be created enzymatically using exohydrolases, endohydrolases or the Sanger method and/or chemically by truncation synthesis or failure sequencing.

It is expected that other approaches can be taken to expand the utility of the CPY/MALDI ladder sequencing methods disclosed herein. For example, by taking advantage of different enzyme specificities, the use of carboxypeptidase mixtures can be implemented using the disclosed on-plate strategy as a means for sequencing through residue combinations that prohibit CPY activity as well as preventing sequence gaps from occurring. Also, by covalently attaching N-terminal linkers to small peptides, it is expected that all sequence peaks can be made to fall beyond the low mass matrix region. It is anticipated that peptides can be completely sequenced to the N-terminus without gaps by combining MALDI with the above-described carboxypeptidase mixtures and mass shift reagent modifications.

It will be apparent to those skilled in the art that various modifications and variations can be made in the compounds and methods of the present invention without departing from the spirit or scope of the invention. Thus, it is intended that the present invention cover the modifications and variations of this invention provided they come within the scope of the appended claims and their equivalents.

What is claimed is:

1. A method of obtaining sequence information about a polymer comprising a plurality of monomers of known mass, said method comprising the steps of:

a) providing a processor in communication with a mass spectrometer;

b) providing a set of polymer fragments, each polymer fragment differing from each other polymer fragment by one or more of the monomers of known mass;

c) measuring a difference x between the mass-to-charge ratio of one pair of polymer fragments with the mass spectrometer;

d) repeating step c) a number of times, n, where n is at least two, using the processor to determine a measured mean mass-to-charge ratio difference. $\bar{x}$, between the pair of polymer fragments;

e) asserting a mean difference, $\mu$, between the mass-to-charge ratio of the pair of polymer fragments measured in step c) using the processor, wherein $\mu$ corresponds to a known mass-to-charge ratio of one monomer of the plurality of monomers of known mass;

f) selecting a desired confidence level for $\mu$;

g) analyzing $\bar{x}$ with the processor to determine if $\bar{x}$ is statistically different from $\mu$ at the selected confidence level;

h) determining with the processor if the asserted mean, $\mu$, is not statistically different from the measured mean mass-to-charge ratio difference, $\bar{x}$, at the selected confidence level based upon the analysis in step g) and if $\mu$ is not statistically different, uniquely assigning one of the pair of polymer fragments to a monomer of the plurality of monomers of known mass corresponding to the mean difference $\mu$;

i) if the asserted mean $\mu$, is statistically different from the measured mean mass-to-charge ratio difference, $\bar{x}$ at the selected confidence level based upon the analysis in step g) then repeating steps e) through h) for a plurality of desired values of $\mu$, each value of $\mu$ corresponding to one monomer of the plurality of monomers of known mass; and j) if after performing step i) a unique assignment of one of the pair of polymer fragments has not been made to one monomer of the plurality of monomers of known mass, then automatically repeating steps d) through i) using the processor and the mass spectrometer for a larger number of times n.

2. The method of claim 1 wherein the analysis in step g) comprises a two-tailed t-test for an experimental mean.

3. The method of claim 1 comprising automatically repeating steps b) through j) for additional sets of polymer fragments using processor and the mass spectrometer.

4. The method of claim 1 wherein the polymer is a biopolymer.

5. The method of claim 4 wherein the biopolymer is selected from the group consisting of DNAs, RNAs, PNAs, proteins, peptides, carbohydrates and modified forms thereof.

6. The method of claim 1 further comprising the step of hydrolyzing the polymer to obtain the polymer fragments in step b).

7. The method of claim 6 wherein the polymer is hydrolyzed on a reaction surface, said surface providing spatially separate differing amounts of a hydrolyzing agent which hydrolyzes said polymer thereby to break inter-monomer bonds.

8. The method of claim 7 wherein the hydrolyzing agent is an exohydrolase.

9. The method of claim 8 wherein hydrolyzing with said exohydrolase produces a series of fragments comprising a sequence-defining ladder of said polymer.

10. The method of claim 9 wherein the exohydrolase is selected from the group consisting of: exonucleases, exoglycosidases, and exopeptidases.

11. The method of claim 10 wherein the exopeptidase is selected from the group consisting of carboxypeptidase Y, carboxypeptidase A, carboxypeptidase B, carboxypeptidase P, aminopeptidase 1, leucine aminopeptidase, proline aminodipeptidase and cathepsin C.

12. The method of claim 10 wherein the exoglycosidase is selected from the group consisting of
   a) α-Mannosidase I
   b) α-Mannosidase
   c) β-Hexosaminodase
   d) β-Galactosidase
   e) α-Fucosidase I and II
   f) α-Galactosidase
   g) α-Neuraminidase and
   h) α-Glucosidase I and II.

13. The method of claim 10 wherein the exonuclease is selected from the group consisting of
   a) λ-exonuclease
   b) t7 Gene 1 exonuclease
   c) exonuclease III
   d) Exonuclease I
   e) Exonuclease V
   f) Exnonuclease II and
   g) DNA Polymerase II.

14. The method of claim 7 wherein the agent is a hydrolyzing agent other than an enzyme.

15. The method of claim 7 wherein the reaction surface comprises a gradient of said hydrolyzing agent.

16. The method of claim 1 further comprising adding a matrix to the polymer fragments before measuring the mass-to-charge ratio in step c).

17. The method of claim 16 wherein the data is analyzed by matrix assisted laser desorption mass spectrometry.

18. A method for obtaining sequence information about a polymer comprising a series of different monomers of known mass, said method comprising the steps of:
   a) hydrolyzing a pole with a hydrolyzing agent wherein the hydrolysis is performed on a reaction surface, said surface providing spatially separate differing amounts of a hydrolyzing agent, said hydrolysis creating a set of polymer fragments, each polymer fragment differing from each other polymer fragment by one or more of the monomers of known mass;
   b) measuring a difference x between the mass-to-charge ratio of one pair of polymer fragments;
   c) repeating step b) a number of times, n, where n is at least two, to determine a measured mean mass-to-charge ratio difference, $\bar{x}$, between the pair of polymer fragments;
   d) asserting a mean difference, $\mu$, between the mass-to-charge ratio of the pair of polymer fragments measured in step b, wherein $\mu$ corresponds to a known mass-to-charge ratio of one of the monomers of known mass;
   e) selecting a desired confidence level for $\mu$;
   f) determining the standard deviation s of the measured mean mass-to-charge ratio difference $\bar{x}$ determined in step c;
   g) calculating a test statistic $t_{calculated}$ with the following algorithm:

$$t_{calculated} = \frac{|\bar{x} - \mu| \sqrt{n}}{s} \; ;$$

h) comparing the test statistic $t_{calculated}$ calculated in step g to a t-distribution corresponding to the number of measurements, n, and the desired confidence level; and
   i) determining if the asserted mean $\mu$ is not substantially different from the measured mean mass-to-charge ratio difference, $\bar{x}$, at the selected confidence level based upon the comparison in step h.

19. The method of claim 18 further comprising repeating steps b)-i) for additional pairs of fragments thereby to obtain sequence information.

20. The method of claim 18 further comprising the step of determining the number of measurements, n, based upon the comparison in step h.

21. The method of claim 18 wherein the polymer is a biopolymer.

22. The method of claim 21 wherein the biopolymer is selected from the group consisting of DNAs, RNAs, PNAs, proteins, peptides, carbohydrates and modified forms thereof.

23. The method of claim 18 wherein the hydrolyzing agent is an exohydrolase which produces a series of fragments comprising a sequence-defining ladder of said polymer.

24. The method of claim 23 wherein the exohydrolase is selected from the group consisting of: exonucleases, exoglycosidases, exopeptidases.

25. The method of claim 24 wherein the exopeptidase is selected from the group consisting of carboxypeptidase Y, carboxypeptidase A, carboxypeptidase B, carboxypeptidase P, aminopeptidase 1, leucine aminopeptidase, proline, aminodipeptidase and cathepsin C.

26. The method of claim 24 wherein the exoglycosidase is selected from the group consisting of
   a) α-Mannosidese I
   b) α-Mannosidese
   c) β-Hexosaminidese
   d) β-Galactosidase
   e) α-Fucosidase I and II
   f) α-Galactosidase
   g) α-Neuraminidase and
   h) α-Glucosidase I and II.

27. The method of claim 24 wherein the exonuclease is selected from the group consisting of
   a) Exonuclease
   b) λ-exonuclease
   c) t7 Gene 1 exonuclease
   d) exonuclease III
   e) Exonuclease I
   f) Exonuclease V g) Exnonuclease II and h) DNA Polymerase II.

28. The method of claim 18 wherein the hydrolyzing agent is other than an enzyme.

29. The method of claim 28 wherein the agent comprises a combination of at least one enzyme and at least one agent other than an enzyme.

30. The method of claim 18 wherein the reaction surface comprises a continuous concentration gradient of a hydrolyzing agent.

31. The method of claim 18 further comprising adding a matrix to the polymer fragments before measuring the mass-to-charge ratio in step b).

32. A method for obtaining sequence information about a polymer having a plurality of monomers of known mass, said method comprising:

a) hydrolyzing a polymer with a hydrolyzing agent wherein the bydrolysis is performed on a reaction surface, said surface providing spatially separate differing amounts of a hydrolyzing agent, said hydrolysis creating a set of polymer fragments, each polymer fragment differing from each other polymer fragment by one or more of the monomers of known mass;

b) determining a measured mean mass-to-charge ratio difference, $\bar{x}$ between one pair of polymer fragments;

c) asserting a mean difference, $\mu$, between the mass-to-charge ratio of the pair of polymer fragments measured in step b, wherein $\mu$ corresponds to a known mass-to-charge ratio of one of the monomers of known mass;

d) selecting the desired confidence level for $\mu$;

e) analyzing $\bar{x}$ to determine if it is statistically different from $\mu$ at the selected confidence level;

f) repeating steps b)–e) a number of times, n, until a plurality of desired values of $\mu$ have been asserted;

g) determining if the asserted mean $\mu$ is not substantially different from the measured mean mass-to-charge ratio difference, $\bar{x}$, at the selected confidence level based upon the analysis in step e; and h) repeating steps b)–g) for additional pairs of fragments.

33. The method of claim 32 wherein the polymer is a biopolymer.

34. The method of claim 33 wherein the biopolymer is selected from the group consisting of DNAs, RNAS, PNAs, proteins, peptides, carbohydrates and modified forms thereof.

35. The method of claim 32 wherein the polymer fragments in step a) are created by concentration dependent hydrolysis of the polymer.

36. The method of claim 32 wherein the hydrolyzing agent is an exohydrolase.

37. The method of claim 36 wherein the hydrolysis caused by said exohydrolase produces a series of fragments defining a ladder of said polymer.

38. The method of claim 36 wherein the exohydrolase is selected from the group consisting of. exonucleases, exoglycosidases, and exopeptidases.

39. The method of claim 38 wherein the exoglycosidase is selected from the group consisting of a) α-Mannosidese I b) α-Mannosidese c) β-Hexosaminidese d) β-Galactosidase e) α-Fucosidase I and II f) α-Galactosidase g) α-Neuraminidase and h) α-Glucosidase I and II.

40. The method of claim 38 wherein the exonuclease is selected from the group consisting of a) Exonuclease b) λ-exonuclease c) t7 Gene 1 exonuclease d) exonuclease III e) Exonuclease I f) Exonuclease V g) Exnonuclease II and h) DNA Polymerase II.

41. The method of claim 38 wherein the exopeptidase is selected from the group consisting of carboxypeptidase Y, carboxypeptidase A, carboxypeptidase B, carboxypeptidase P, aminopeptidase 1, leucine aminopeptidase, proline, aminodipeptidase and cathepsin C.

42. The method of claim 32 wherein said agent comprises a hydrolyzing agent other than an enzyme.

43. The method of claim 32 wherein the polymer fragments are obtained by hydrolysis with a combination of at least one enzyme and at least one hydrolyzing agent other than an enzyme.

44. The method of claim 32 wherein the reaction surface comprises a concentration gradient of said hydrolyzing agent.

45. The method of claim 32 further comprising adding a matrix to the polymer fragments before measuring the mass-to-charge ratio in step b).

46. The method of claim 1 wherein multiple different sets of polymer fragments obtained from the same polymer are provided in step b).

47. The method of claim 1 further comprising the step of eluting from a liquid chromatography column a sample comprising the polymer for which sequence information is to be obtained.

* * * * *

UNITED STATES PATENT AND TRADEMARK OFFICE
CERTIFICATE OF CORRECTION

PATENT NO. : 5,869,240
DATED : February 9, 1999
INVENTOR(S) : Dale H. patterson

It is certified that error appears in the above-identified patent and that said Letters Patent is hereby corrected as shown below:

Claim 3, line 3, between "using" and "processor" insert ---the---.
Claim 18, line 4, delete "pole" and insert ---polymer---.
Claim 32, line 5, delete "bydrolysis" and insert ---hydrolysis---.
Claim 34, line 2, delete "RNAS" and insert ---RNAs---.
Claim 38, line 2, after "of" delete the period and insert a colon.

Signed and Sealed this

Thirteenth Day of July, 1999

Attest:

Q. TODD DICKINSON

Attesting Officer

Acting Commissioner of Patents and Trademarks

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide (x i) SEQUENCE DESCRIPTION: SEQ ID NO:1:

Trp Ala Gly Gly Asp Ala Ser Gly Glu
1               5

(2) INFORMATION FOR SEQ ID NO:2:

(i) SEQUENCE CHARACTERISTICS:
    (A) LENGTH: 8 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:2:

Val His Leu Thr Pro Val Glu Lys
1               5

(2) INFORMATION FOR SEQ ID NO:3:

(i) SEQUENCE CHARACTERISTICS:
    (A) LENGTH: 9 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:3:

Val Gln Gly Glu Glu Ser Asn Asp Lys
1               5

(2) INFORMATION FOR SEQ ID NO:4:

(i) SEQUENCE CHARACTERISTICS:
    (A) LENGTH: 8 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:4:

Lys Arg Gln His Pro Gly Lys Arg
1               5

(2) INFORMATION FOR SEQ ID NO:5:

(i) SEQUENCE CHARACTERISTICS:
    (A) LENGTH: 9 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:5:

Arg Pro Pro Gly Phe Ser Pro Phe Arg
1               5

(2) INFORMATION FOR SEQ ID NO:6:

(i) SEQUENCE CHARACTERISTICS:
    (A) LENGTH: 10 amino acids
    (B) TYPE: amino acid
    (C) STRANDEDNESS: single
    (D) TOPOLOGY: linear (i i) MOLECULE TYPE: peptide ( x i ) SEQUENCE DESCRIPTION: SEQ ID NO:6:

Glu His Trp Ser Tyr Gly Leu Arg Pro Gly
1               5                   10

( 2 ) INFORMATION FOR SEQ ID NO:7:

( i ) SEQUENCE CHARACTERISTICS:
     ( A ) LENGTH: 11 amino acids
     ( B ) TYPE: amino acid
     ( C ) STRANDEDNESS: single
     ( D ) TOPOLOGY: linear ( i i ) MOLECULE TYPE: peptide ( x i ) SEQUENCE DESCRIPTION: SEQ ID NO:7:

Glu Ala Asp Pro Asn Lys Phe Tyr Gly Leu Met
1               5                   10

( 2 ) INFORMATION FOR SEQ ID NO:8:

( i ) SEQUENCE CHARACTERISTICS:
     ( A ) LENGTH: 10 amino acids
     ( B ) TYPE: amino acid
     ( C ) STRANDEDNESS: single
     ( D ) TOPOLOGY: linear ( i i ) MOLECULE TYPE: peptide ( x i ) SEQUENCE DESCRIPTION: SEQ ID NO:8:

Asp Arg Val Tyr Ile His Pro Phe His Leu
1               5                   10

( 2 ) INFORMATION FOR SEQ ID NO:9:

( i ) SEQUENCE CHARACTERISTICS:
     ( A ) LENGTH: 10 amino acids
     ( B ) TYPE: amino acid
     ( C ) STRANDEDNESS: single
     ( D ) TOPOLOGY: linear ( i i ) MOLECULE TYPE: peptide ( x i ) SEQUENCE DESCRIPTION: SEQ ID NO:9:

Pro His Pro Phe His Phe Phe Val Tyr Lys
1               5                   10

( 2 ) INFORMATION FOR SEQ ID NO:10:

( i ) SEQUENCE CHARACTERISTICS:
     ( A ) LENGTH: 12 amino acids
     ( B ) TYPE: amino acid
     ( C ) STRANDEDNESS: single
     ( D ) TOPOLOGY: linear ( i i ) MOLECULE TYPE: peptide ( x i ) SEQUENCE DESCRIPTION: SEQ ID NO:10:

Asp Val Pro Lys Ser Asp Gln Phe Val Gly Leu Met
1               5                   10

( 2 ) INFORMATION FOR SEQ ID NO:11:

( i ) SEQUENCE CHARACTERISTICS:
     ( A ) LENGTH: 11 amino acids
     ( B ) TYPE: amino acid
     ( C ) STRANDEDNESS: single
     ( D ) TOPOLOGY: linear ( i i ) MOLECULE TYPE: peptide (x i) SEQUENCE DESCRIPTION: SEQ ID NO:11:

```
Arg  Pro  Lys  Pro  Gln  Gln  Phe  Phe  Gly  Leu  Met
1                   5                        10
```

(2) INFORMATION FOR SEQ ID NO:12:

(i) SEQUENCE CHARACTERISTICS:
        (A) LENGTH: 13 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:12:

```
Cys  Gly  Tyr  Gly  Pro  Lys  Lys  Lys  Arg  Lys  Val  Gly  Gly
1                   5                        10
```

(2) INFORMATION FOR SEQ ID NO:13:

(i) SEQUENCE CHARACTERISTICS:
        (A) LENGTH: 13 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:13:

```
Gly  Ala  Pro  Val  Pro  Tyr  Pro  Asp  Pro  Leu  Glu  Pro  Arg
1                   5                        10
```

(2) INFORMATION FOR SEQ ID NO:14:

(i) SEQUENCE CHARACTERISTICS:
        (A) LENGTH: 16 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:14:

```
Ala  Asp  Ser  Gly  Glu  Gly  Asp  Phe  Leu  Ala  Glu  Gly  Gly  Gly  Val  Arg
1                   5                        10                       15
```

(2) INFORMATION FOR SEQ ID NO:15:

(i) SEQUENCE CHARACTERISTICS:
        (A) LENGTH: 13 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:15:

```
Gly  Glu  Gln  Arg  Lys  Asp  Val  Tyr  Val  Gln  Leu  Tyr  Leu
1                   5                        10
```

(2) INFORMATION FOR SEQ ID NO:16:

(i) SEQUENCE CHARACTERISTICS:
        (A) LENGTH: 14 amino acids
        (B) TYPE: amino acid
        (C) STRANDEDNESS: single
        (D) TOPOLOGY: linear (i i) MOLECULE TYPE: peptide ( x i ) SEQUENCE DESCRIPTION: SEQ ID NO:16:

Glu Gln Arg Leu Gly Asn Gln Trp Ala Val Gly His Leu Met
1               5                   10

( 2 ) INFORMATION FOR SEQ ID NO:17:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

Lys Pro Val Gly Lys Lys Arg Arg Pro Val Lys Val Tyr Pro
1               5                   10

( 2 ) INFORMATION FOR SEQ ID NO:18:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

Ser Thr Ser Met Glu His Phe Arg Trp Gly Lys Pro Val
1               5                   10

( 2 ) INFORMATION FOR SEQ ID NO:19:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

Asp Arg Val Tyr Ile His Pro Phe His Leu Leu Val Tyr Ser
1               5                   10

( 2 ) INFORMATION FOR SEQ ID NO:20:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

Glu Asn Gly Leu Pro Val His Leu Asp Gln Ser Ile Phe Arg Arg
1               5                   10                  15

( 2 ) INFORMATION FOR SEQ ID NO:21:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

( 2 ) INFORMATION FOR SEQ ID NO:22:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

Phe Arg Trp Gly Lys Pro Val Gly Lys Lys Arg Arg Pro Val Lys Val
1               5                   10                  15

Tyr Pro Asn Gly Ala Glu Asp Glu Ser Ala Glu Ala Phe Pro Leu Glu
            20                  25                  30

( 2 ) INFORMATION FOR SEQ ID NO:23:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "NUCLEIC ACID POLYMER"

( x i ) SEQUENCE DESCRIPTION: SEQ ID NO:23:

CGCTCTCCCT TATGCGACTC CTGCATTAGG AAGCAGCCCA  40